Figure 1A:
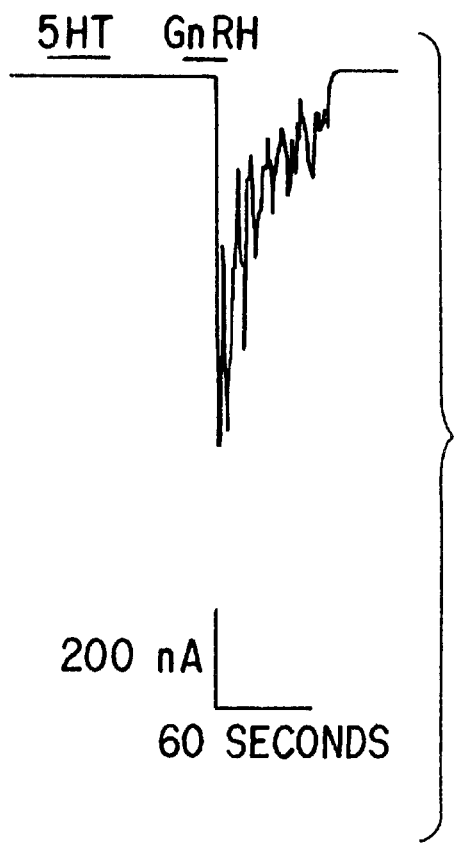

United States Patent [19]

Sealfon

[11] Patent Number: 5,985,583
[45] Date of Patent: Nov. 16, 1999

[54] CLONING AND EXPRESSION OF GONADOTROPIN-RELEASING HORMONE RECEPTOR

[75] Inventor: Stuart C. Sealfon, Brooklyn Heights, N.Y.

[73] Assignee: Mount Sinai School of Medicine of The City University of New York, New York, N.Y.

[21] Appl. No.: 08/390,000

[22] Filed: Feb. 17, 1995

Related U.S. Application Data

[63] Continuation-in-part of application No. 08/080,386, Jun. 21, 1993, Pat. No. 5,750,366, which is a continuation-in-part of application No. 07/904,072, Jun. 23, 1992, abandoned.

[51] Int. Cl.$^6$ ............ C07K 14/72; G01N 33/566; C12N 15/10; C12N 5/10
[52] U.S. Cl. ............ 435/7.2; 435/7.21; 435/325; 435/69.1; 435/252.3; 435/254.11; 530/399
[58] Field of Search ............ 436/501; 435/7.8, 435/7.1, 7.21, 240.2, 172.3, 325, 69.1, 252.3, 254.11; 530/399

[56] References Cited

U.S. PATENT DOCUMENTS

| | | | |
|---|---|---|---|
| 4,618,598 | 10/1986 | Conn | 514/6 |
| 5,064,939 | 11/1991 | Rivier et al. | 530/317 |

OTHER PUBLICATIONS

Wright et al., Cloning stratagies for peptide hormone receptors, Acta Endocrinologica, 126: 97–104, Mar. 1992.
Titus, Ed., Promega Protocols and Applications Guide, 2nd ed., pp. 297–305, Mar. 1991.
Clayton, 1987, "Gonadotrophin Releasing Hormone: from Physiology to Pharmacology," Clinical Endocrinology 26:361–384.
Clayton, 1989, "Gonadotrophin–Releasing Hormone: its Actions and Receptors," Journal of Endocrinology 120:11–19.
Sealfon et al., 1990, "Gonadotropin–Releasing Hormone Receptor Expression in Xenopus Oocytes," Molecular Endocrinology 4:119–124.
Probst et al., 1992, "Sequence Alignment of the G–Protein Coupled Receptor Superfamily," DNA and Cell Biology 11:1–20.
Tsutsumi et al., 1992, "Cloning and Functional Expression of a Mouse Gonadotropin–Releasing Hormone Receptor," Molecular Endocrinology 6(7):1163–1169.

Eidne et al., 1992, "Molecular Cloning and Characterization of the Rat Pituitary Gonadotropin–Releasing Hormone (GnRH) Receptor," Molecular and Cellular Endocrinology 90:R5–R9.
Kakar et al., 1992 "Cloning, Sequencing and Expression of Human Gonadotropin Releasing Hormone (GnRH) Receptor," Biochemical and Biophysical Research Communications 189(1):289–295.
Chi et al., 1993, "Cloning and Characterization of the Human GnRH Receptor," Molecular and Cellular Endocrinology 91:R1–R6.
Sealfon et al. (1990) Hormonal Regulation of Gonadotropin–Releasing Hormone Receptors and Messenger RNA Activity in Ovine Pituitary Culture, Mol. Endocrinol. 4: 1980–1987.
Hawes et al. (1992) Development of Gonadotrope Desensitization to Gonadotropin–Releasing Hormone (GnRH) and Recovery Are Not Coupled to Inositol Phosphate Production or GnRH Receptor Number, Endocrinol. 131: 2681–2689.
McArdle et al., Estradiol regulates gonadotropin–releasing hormone receptor number, growth and inositol phosphate production in alphT3–1 cells, Mol. Cell. Endocrinol., 87: 95–103, 1992.
Horn et al., Intracellular response to gonadotropin–releasing hormone in a clonal cell line of the gonadotrope lineage, Mol. Endocrinol., 5: 347–355, 1991.
Windle et al., Cell lines of the pituitary gonadotrope lineage derived by targeted oncogenesis in transgenic mice, Mol. Endocrinol. 4: 597–603, 1990.

*Primary Examiner*—Lila Feisee
*Assistant Examiner*—Claire M. Kaufman
*Attorney, Agent, or Firm*—Pennie & Edmonds LLP

[57] ABSTRACT

The present invention relates to the GnRH-R genes and proteins. The DNA sequence disclosed herein may be engineered into expression systems designed for the production of GnRH-R and/or cell lines which express the GnRH-R and preferably respond to GnRH induced signal transduction. Such cell lines may advantageously be used for screening and identifying GnRH agonists and antagonists. In accordance with another aspect of the invention, the GnRH DNA, antisense oligonucleotide sequences, the GnRH expression products, and antibodies to such products may be used in the diagnosis and therapy of reproductive disorders associated with abnormal expression of the GnRH-R; e.g., overexpression, underexpression or expression of a dysfunctional mutant receptor. Transgenic animals containing the GnRH-R transgene may be used as animal models for the evaluation of GnRH analogs in vivo.

4 Claims, 16 Drawing Sheets

```
                    CACGAGAGGGACTCCACTCTTGAAGCCTGTCCTTGGAGAAAT      -1

ATGGCTAACAATGCATCTCTTGAGCAGGACCCAAATCACTGCTCGGCCATCAACAACAGC      60
 M  A  N  N  A  S  L  E  Q  D  P  N  H  C  S  A  I  N  N  S       20

ATCCCCTTGATACAGGGCAAGCTCCCGACTCTAACCGTATCTGGAAAGATCCGAGTGACC     120
 I  P  L  I  Q  G  K  L  P  T  L  T  V  S  G  K  I  R  V  T       40

GTGACTTTCTTCCTTTTCCTACTCTCTACTGCCTTCAATGCTTCCTTCTTGTTGAAGCTG     180
 V  T  F  F  L  F  L  L  S  T  A  F  N  A  S  F  L  L  K  L       60
                              I

CAGAAGTGGACTCAGAAGAGGAAGAAAGGAAAAAAGCTCTCAAGGATGAAGGTGCTTTTA     240
 Q  K  W  T  Q  K  R  K  K  G  K  K  L  S  R  M  K  V  L  L       80

AAGCATTTGACCTTAGCCAACCTGCTGGAGACTCTGATCGTCATGCCACTGGATGGGATG     300
 K  H  L  T  L  A  N  L  L  E  T  L  I  V  M  P  L  D  G  M      100
                              II

TGGAATATTACTGTTCAGTGGTATGCTGGGGAGTTCCTCTGCAAAGTTCTCAGCTATCTG     360
 W  N  I  T  V  Q  W  Y  A  G  E  F  L  C  K  V  L  S  Y  L      120

AAGCTCTTCTCTATGTATGCCCCAGCTTTCATGATGGTGGTGATTAGCCTGGACCGCTCC     420
 K  L  F  S  M  Y  A  P  A  F  M  M  V  V  I  S  L  D  R  S      140
       III

CTGGCCATCACTCAGCCCCTTGCTGTACAAAGCAACAGCAAGCTTGAACAGTCTATGATC     480
 L  A  I  T  Q  P  L  A  V  Q  S  N  S  K  L  E  Q  S  M  I      160

AGCCTGGCCTGGATTCTCAGCATTGTCTTTGCAGGACCACAGTTATATATCTTCAGGATG     540
 S  L  A  W  I  L  S  I  V  F  A  G  P  Q  L  Y  I  F  R  M      180
            IV

ATCTACCTAGCAGACGGCTCTGGGCCCACAGTCTTCTCGCAATGTGTGACCCACTGCAGC     600
 I  Y  L  A  D  G  S  G  P  T  V  F  S  Q  C  V  T  H  C  S      200

TTTCCACAGTGGTGGCATCAGGCCTTCTACAACTTTTTCACCTTCGGCTGCCTCTTCATC     660
 F  P  Q  W  W  H  Q  A  F  Y  N  F  F  T  F  G  C  L  F  I      220
                                V

ATCCCCCTCCTCATCATGCTAATCTGCAATGCCAAAATCATCTTTGCTCTCACGCGAGTC     720
 I  P  L  L  I  M  L  I  C  N  A  K  I  I  F  A  L  T  R  V      240

CTTCATCAAGACCCACGCAAACTACAGATGAATCAGTCCAAGAATAATATCCCAAGAGCT     780
 L  H  Q  D  P  R  K  L  Q  M  N  Q  S  K  N  N  I  P  R  A      260
```

FIG.3A

```
CGGCTGAGAACGCTAAAGATGACAGTCGCATTCGCTACCTCCTTTGTCGTCTGCTGGACT  840
 R  L  R  T  L  K  M  T  V  A  F  A  T  S  F  V  V  C  W  T   280
       *                ─────────────────────────────────── VI ──

CCCTACTATGTCCTAGGCATTTGGTACTGGTTTGATCCAGAAATGTTGAACAGGGTGTCA  900
 P  Y  Y  V  L  G  I  W  Y  W  F  D  P  E  M  L  N  R  V  S   300
 ─────────────────────────

GAGCCAGTGAATCACTTTTTCTTTCTCTTTGCTTTCCTAAACCCGTGCTTCGACCCACTC  960
 E  P  V  N  H  F  F  F  L  F  A  F  L  N  P  C  F  D  P  L   320
       ──────────────────── VII ──────────────────────────────

ATATATGGGTATTTCTCTTTGTAGTTGGGAGACTACACAAGAACTCAGATAGAAATAAGG 1020
 I  Y  G  Y  F  S  L                                          327
 ──────────────────

TAACTAATTGCACCAATTGAGAATAAACTCAAAGCTTTTGACACACTTATATACAAGGCA 1080
GGGTTTAAGGTTAGATTATCAACCTTGTTTTTGTACAGAGTTTGTTGTTAGAGCTTCAGA 1140
AGACCTTCAAAAACAAAAAAAAAAAAAAAAAAAAAAAAAAAAAAA                1185
```

FIG. 3B

```
                                                                                                              I
GnR                                          MANNASLEQDPNHCSAINNSIPLIQGKLPTLTVSGKIRMTVTFFLFLLSTAFNASFLLKLQKWTQKR
ILR                         MESDSFEDFWKGEDLSNYSYSSTLPPFLLDAAPCEPESLEINKYFVMIIYALVFLLSLLGNSLVMLVILYSRVGR
SPR                                   MDNVLPMDSDLFPNISTNTSESNQFVQPTWQIVLWAAAYTVIVVTSVVGNVVVIWIILAHKRMR
β1R      (9)ASEPGNLSSAAPLPDGAATAARLLVPASPPASLLPBASESPEPLSQQWTAGMGLLMALIVLLITVAGNVLVIVAIAKTPRLQ
RHO                                     MNGTEGPNFYVPFSNATGVVRSPFEYPQYLAEPWQFSMLAAYM-FLIVLGFPINFLTYVTVQHKKLR

III
GnR      KKGKKLSRMKVLLKHLTLANLLETLIIVMPLDGMWNITVQWYAGEFLCKVLSYLKLFSMYAPAFMMVISLDRSLATTQPLAVQSN
ILR      SVTD-----VYLLNLALADLLFALTLPIWAASKVNGWIF--GTFLCKVWSLLKEVNFYSGILLLACISVDRYLAIVHATRTLTQ
SPR      TVTN-----YFLVVNLAFAEACMAAFNTVVNFTYAVHNVWYYGLFFYCKFHNFFPIAALFASIYSMTAVAFDRYMAILHPLQPRLS
β1R      TLTN-----LFIMSLASADLVMGLLVMPFGATIVVWGRWEYGSFFCELWTSVDVLCVTASIETLCVIALDRYLAITSPFRYQSL
RHO      TPLN-----YILLNLAVADLFMVLGGFTSTLYTSLHGYFVFGPTGCNLEGFFATLGGEIALWSLVVLAIERYVVVCKPMSNFRF

V
GnR      --SKLEQSMISLAWILSIVFAGPQLYIFRMIYLADGSGPTVFSQCVTH-CSFQWWHQAFYNFFTEGCLFITPLLIMLICNAKIIFALTR
ILR      -KRYLVKFICLSIWGLSLLLALPVLCFRRTVYSSN-----VSPACYED-MGNNTANWRMLRILPQSFGEIVPLLIMLFCYGFTLRTLFK
SPR      --ATATKVVIFVIWVLALLLAFPQGMYSTTETMPS------RVVCMIEWPEHPNRTYEKAMHICVTVLIYFLPLLVIAYAYTVVGITLWA
β1R      LTRARARGLVCTVWAISALVSFLPILMHWWRAESD------EARRCYNDPKCCD-FVTNRAYAIASSVVSFYVPLCIMAFVYLRVFREAQK
RHO      -GENHAIMGVAFTWVMALACAAPPLAGWSRYIPEG------LQCSCGIDYTLKPEVNNESFVIYMEVVHFIIPMIIFFCYGQLVETVKE
```

FIG. 4B

```
                                        VI
GnR    VLHQD------------------------PRKLQMNQSKNNIPRARLRTLKMTVAFATSFVVCWTPYYVLGIWYWFDPEMLNRV
ILR    AHMGQ--------------------------KHRAMRVIFAVVLIFLLCWLPYNLVLLADTLMRTQVIQE
SPR    SEIPG--------------------------DSSDRYHEQVSAKRKVVKMIVVCTFAICWLPFHVFFLLPYINDLYLKK
β1R    QVKKIDSCERRFLGGPARPPSPSP.(20).TAPLANGRAGKRRPSRLVALREQKALKTLGIIMGVFTLCWLPEFLANVVKAEH
RHD    -------------------------------AAAQQQESATTQKAEKEVTRMVIIMVIAFLICWVPYASVAFYIFTHQGSNFGPI

VII
GnR    ------SEPVNHEEFLEAFLNPCEDPLIYGYFSL
ILR    TCERRNHIDRALDATEILGILHSCLNPLIYAFIGQKFRHGLLKILAIHGLISKDSLPKDSRPSFVGSSSGHTSTTL
SPR    ------FIQQVYLASMWLAMSSTMYNPIIYCCLNDRFRLGFKHAFRCCPFISAGDYEGLEMKSTRYLQTQSSVYKVSRLETTISTVVG(43)
β1R    ------RELVPDRLFVEENWLGYANSAENPIIYCRSPDFRKAFQGLLCCARRAARRRHATHGDRPRASGCLARPPPSPGAASDDDDDDV(43)
RHD    ------FMTIPAFFAKSAAIYNPVIYIMMNKQFRNCMLTTICCGKNPLGDDEASATVSKTETSQVAPA
```

FIG.4C

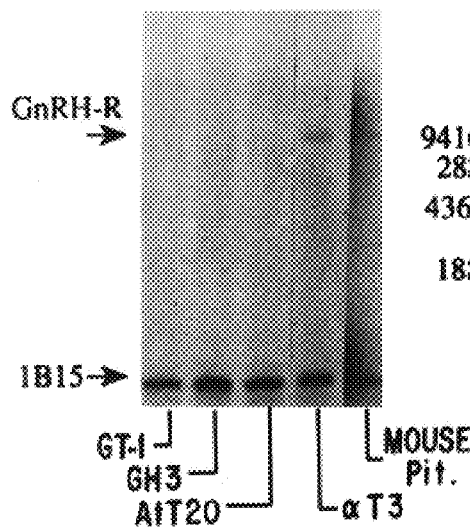
FIG. 5A
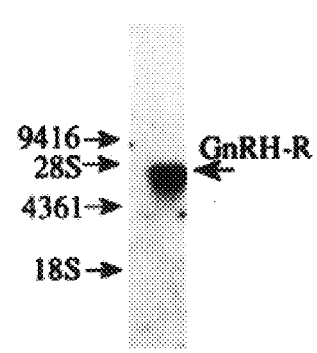
FIG. 5B
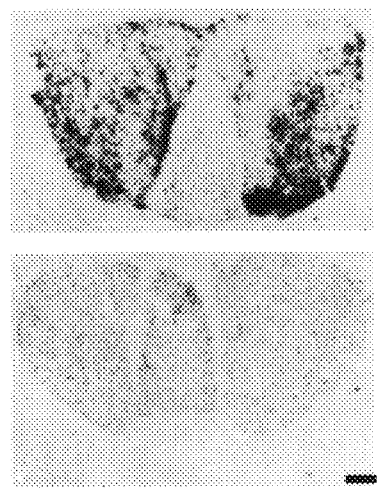
FIG. 5C
FIG. 5D
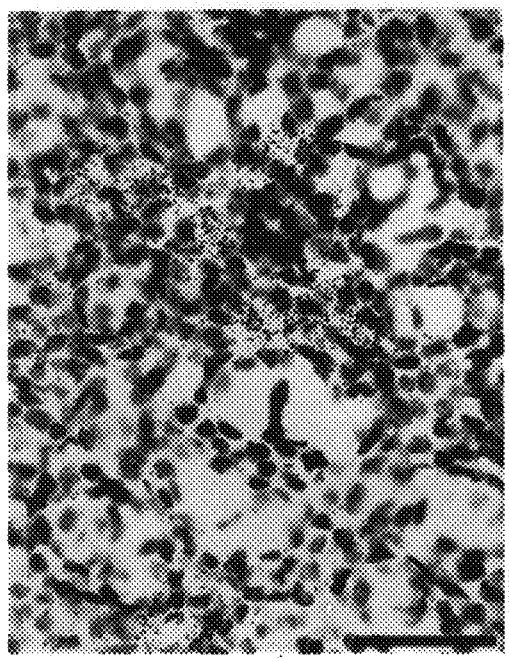
FIG. 5E
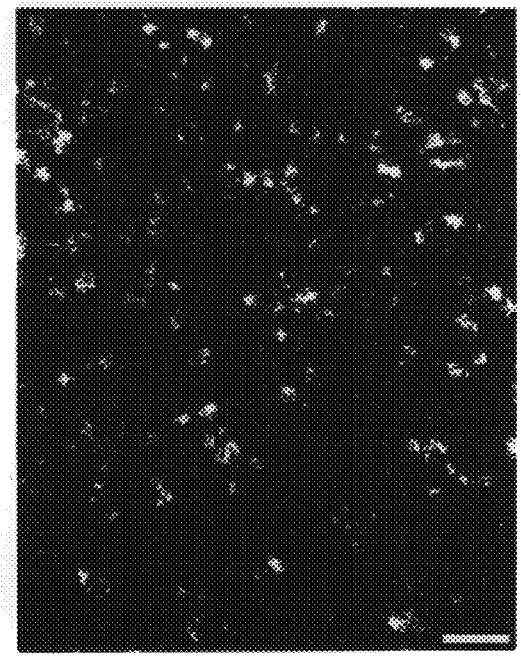
FIG. 5F

```
                                              CGGAGCCTTGTGTCCTGGGAAAAT    -1
ATGGCAAACAGTGCCTCTCCTGAACAGAATCAAAATCACTGTTCAGCCATCAACAACAGC            60
 M  A  N  S  A  S  P  E  Q  N  Q  N  H  C  S  A  I  N  N  S            20
ATCCCACTGATGCAGGGCAACCTCCCCACTCTGACCTTGTCTGGAAAGATCCGAGTGACG           120
 I  P  L  M  Q  G  N  L  P  T  L  T  L  S  G  K  I  R  V  T            40
GTTACTTTCTTCCTTTTTCTGCTCTCTGCGACCTTTAATGCTTCTTTCTTGTTGAAACTT           180
 V  T  F  F  L  F  L  L  S  A  T  F  N  A  S  F  L  L  K  L            60
CAGAAGTGGACACAGAAGAAAGAGAAAGGGAAAAAGCTCTCAAGAATGAAGCTGCTCTTA           240
 Q  K  W  T  Q  K  K  E  K  G  K  K  L  S  R  M  K  L  L  L            80
AAACATCTGACCTTAGCCAACCTGTTGGAGACTCTGATTGTCATGCCACTGGATGGGATG           300
 K  H  L  T  L  A  N  L  L  E  T  L  I  V  M  P  L  D  G  M           100
TGGAACATTACAGTCCAATGGTATGCTGGAGAGTTACTCTGCAAAGTTCTCAGTTATCTA           360
 W  N  I  T  V  Q  W  Y  A  G  E  L  L  C  K  V  L  S  Y  L           120
AAGCTTTTCTCCATGTATGCCCCAGCCTTCATGATGGTGGTGATCAGCCTGGACCGCTCC           420
 K  L  F  S  M  Y  A  P  A  F  M  M  V  V  I  S  L  D  R  S           140
CTGGCTATCACGAGGCCCCTAGCTTTGAAAAGCAACAGCAAAGTCGGACAGTCCATGGTT           480
 L  A  I  T  R  P  L  A  L  K  S  N  S  K  V  G  Q  S  M  V           160
GGCCTGGCCTGGATCCTCAGTAGTGTCTTTGCAGGACCACAGTTATACATCTTCAGGATG           540
 G  L  A  W  I  L  S  S  V  F  A  G  P  Q  L  Y  I  F  R  M           180
ATTCATCTAGCAGACAGCTCTGGACAGACAAAAGTTTTCTCTCAATGTGTAACACACTGC           600
 I  H  L  A  D  S  S  G  Q  T  K  V  F  S  Q  C  V  T  H  C           200
AGTTTTTCACAATGGTGGCATCAAGCATTTTATAACTTTTTCACCTTCAGCTGCCTCTTC           660
 S  F  S  Q  W  W  H  Q  A  F  Y  N  F  F  T  F  S  C  L  F           220
ATCATCCCTCTTTTCATCATGCTGATCTGCAATGCAAAAATCATCTTCACCCTGACACGG           720
 I  I  P  L  F  I  M  L  I  C  N  A  K  I  I  F  T  L  T  R           240
GTCCTTCATCAGGACCCCCACGAACTACAACTGAATCAGTCCAAGAACAATATACCAAGA           780
 V  L  H  Q  D  P  H  E  L  Q  L  N  Q  S  K  N  N  I  P  R           260
GCACGGCTGAAGACTCTAAAAATGACGGTTGCATTTGCCACTTCATTTACTGTCTGCTGG           840
 A  R  L  K  T  L  K  M  T  V  A  F  A  T  S  F  T  V  C  W           280
ACTCCCTACTATGTCCTAGGAATTTGGTATTGGTTTGATCCTGAAATGTTAAACAGGTTG           900
 T  P  Y  Y  V  L  G  I  W  Y  W  F  D  P  E  M  L  N  R  L           300
TCAGACCCAGTAAATCACTTCTTCTTTCTCTTTGCCTTTTTAAACCCATGCTTTGATCCA           960
 S  D  P  V  N  H  F  F  F  L  F  A  F  L  N  P  C  F  D  P           320
CTTATCTATGGATATTTTCTCTGTGATTGATAGACTACACAAGAAGTCATATGAAGAAG          1020
 L  I  Y  G  Y  F  S  L  *                                             328
GGTAAGGTAATGAATCTCTCCATCTGGGAATGATTAACACAAATGTTGGAGCATGTTTAC          1080
ATACAAACAAAGTAGGATTTACACTTAAGTTATCATTCTTTTAGAAACTCAGTCTTCAGA          1140
GCCTCAATTATTAAGGAAAAGTCTTCAGGAAAAATACTAAAATATTTTCTCTTCCTCATA          1200
AGCTTCTAAATTAATCTCTGCCTTTTCTGACCTCATATAACACATTATGTAGGTTTCTTA          1260
```

FIG.9A

```
TCACTTTCTCTTTGCATAATAATGTACTAATATTTAAAATACCTTCAGCCTAAGGCACAA    1320
GGATGCCAAAAAAACAAAGGTGAGAACCCACAACACAGGTCTAAACTCAGCATGCTTGGT    1380
GAGTTTTTCTCCAAAGGGGCATATTAGCAATTAGAGTTGTATGCTATATAATACATAGAG    1440
CACAGAGCCCTTTGCCCATAATATCAACTTTCCCTCCTATAGTTAAAAAGAAAAAAAAAT    1500
GAATCTATTTTTCTCTTTGGCTTCAAAAGCATTCTGACATTTGGAGGAGTCAGTAACCAA    1560
TCCCACCAACCACTCCAGCAACCTGACAAGACTATGAGTAGTTCTCCTTCATCCTATTTA    1620
TGTGGTACAGGTTGTGAAGTATCTCTATATAAAGGGAAATTTTAGAGGGGTTAGGATTTG    1680
GACAGGGGTTTAGAACATTCCTCTAAGCTATCTAGTCTGTGGAGTTTGTGGCAATTAATT    1740
GCCATAAAATAACATGTTTCCAAATGCAACTAAGAAAATACTCATAGTGAGTACGCTCTA    1800
TGCATAGTATGACTTCTATTTAATGTGAAGAATTTTTTGTCTCTCTCCTGATCTTACTAA    1860
ATCCATATTTCATAAATGAACTGAGAATAATTAACAAAATTAAGCAAATGCACAAGCAAA    1920
AGATGCTTGATACACAAAAGGAACTCTGGAGAGAAAACTACAGCTTCAGTCTGTACAGAT    1980
CAAAGAAGACAGAACATGTCAGGGGAAGGAGGAAAGATCTTGATGCAGGGTTTCTTAACC    2040
TGCAGTCTATGCACAACACTATATTTCCATGTAATGTTTTTATTTCAGCCCTATTTGTAT    2100
TATTTTGTGCATTTAAAAAACACAATCTTAAGGCCG                            2136
```

FIG.9B

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 1227 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 43..1023

(xi) SEQUENCE DESCRIPTION: SEQ ID NO:1:

```
CACGAGAGGG ACTCCACTCT TGAAGCCTGT CCTTGGAGAA AT ATG GCT AAC AAT        54
                                              Met Ala Asn Asn
                                                1

GCA TCT CTT GAG CAG GAC CCA AAT CAC TGC TCG GCC ATC AAC AAC AGC      102
Ala Ser Leu Glu Gln Asp Pro Asn His Cys Ser Ala Ile Asn Asn Ser
 5                  10                  15                  20

ATC CCC TTG ATA CAG GGC AAG CTC CCG ACT CTA ACC GTA TCT GGA AAG      150
Ile Pro Leu Ile Gln Gly Lys Leu Pro Thr Leu Thr Val Ser Gly Lys
                25                  30                  35

ATC CGA GTG ACC GTG ACT TTC TTC CTT TTC CTA CTC TCT ACT GCC TTC      198
Ile Arg Val Thr Val Thr Phe Phe Leu Phe Leu Leu Ser Thr Ala Phe
                    40                  45                  50

AAT GCT TCC TTC TTG TTG AAG CTG CAG AAG TGG ACT CAG AAG AGG AAG      246
Asn Ala Ser Phe Leu Leu Lys Leu Gln Lys Trp Thr Gln Lys Arg Lys
                55                  60                  65

AAA GGA AAA AAG CTC TCA AGG ATG AAG GTG CTT TTA AAG CAT TTG ACC      294
Lys Gly Lys Lys Leu Ser Arg Met Lys Val Leu Leu Lys His Leu Thr
 70                  75                  80

TTA GCC AAC CTG CTG GAG ACT CTG ATC GTC ATG CCA CTG GAT GGG ATG      342
Leu Ala Asn Leu Leu Glu Thr Leu Ile Val Met Pro Leu Asp Gly Met
 85                  90                  95                 100

TGG AAT ATT ACT GTT CAG TGG TAT GCT GGG GAG TTC CTC TGC AAA GTT      390
Trp Asn Ile Thr Val Gln Trp Tyr Ala Gly Glu Phe Leu Cys Lys Val
                    105                 110                 115

CTC AGC TAT CTG AAG CTC TTC TCT ATG TAT GCC CCA GCT TTC ATG ATG      438
Leu Ser Tyr Leu Lys Leu Phe Ser Met Tyr Ala Pro Ala Phe Met Met
                    120                 125                 130
```

```
GTG GTG ATT AGC CTG GAC CGC TCC CTG GCC ATC ACT CAG CCC CTT GCT        486
Val Val Ile Ser Leu Asp Arg Ser Leu Ala Ile Thr Gln Pro Leu Ala
        135                 140                 145

GTA CAA AGC AAC AGC AAG CTT GAA CAG TCT ATG ATC AGC CTG GCC TGG        534
Val Gln Ser Asn Ser Lys Leu Glu Gln Ser Met Ile Ser Leu Ala Trp
150                 155                 160

ATT CTC AGC ATT GTC TTT GCA GGA CCA CAG TTA TAT ATC TTC AGG ATG        582
Ile Leu Ser Ile Val Phe Ala Gly Pro Gln Leu Tyr Ile Phe Arg Met
165                 170                 175                 180

ATC TAC CTA GCA GAC GGC TCT GGG CCC ACA GTC TTC TCG CAA TGT GTG        630
Ile Tyr Leu Ala Asp Gly Ser Gly Pro Thr Val Phe Ser Gln Cys Val
                185                 190                 195

ACC CAC TGC AGC TTT CCA CAG TGG TGG CAT CAG GCC TTC TAC AAC TTT        678
Thr His Cys Ser Phe Pro Gln Trp Trp His Gln Ala Phe Tyr Asn Phe
                    200                 205                 210

TTC ACC TTC GGC TGC CTC TTC ATC ATC CCC CTC CTC ATC ATG CTA ATC        726
Phe Thr Phe Gly Cys Leu Phe Ile Ile Pro Leu Leu Ile Met Leu Ile
                215                 220                 225

TGC AAT GCC AAA ATC ATC TTT GCT CTC ACG CGA GTC CTT CAT CAA GAC        774
Cys Asn Ala Lys Ile Ile Phe Ala Leu Thr Arg Val Leu His Gln Asp
230                 235                 240

CCA CGC AAA CTA CAG ATG AAT CAG TCC AAG AAT AAT ATC CCA AGA GCT        822
Pro Arg Lys Leu Gln Met Asn Gln Ser Lys Asn Asn Ile Pro Arg Ala
245                 250                 255                 260

CGG CTG AGA ACG CTA AAG ATG ACA GTC GCA TTC GCT ACC TCC TTT GTC        870
Arg Leu Arg Thr Leu Lys Met Thr Val Ala Phe Ala Thr Ser Phe Val
                265                 270                 275

GTC TGC TGG ACT CCC TAC TAT GTC CTA GGC ATT TGG TAC TGG TTT GAT        918
Val Cys Trp Thr Pro Tyr Tyr Val Leu Gly Ile Trp Tyr Trp Phe Asp
                280                 285                 290

CCA GAA ATG TTG AAC AGG GTG TCA GAG CCA GTG AAT CAC TTT TTC TTT        966
Pro Glu Met Leu Asn Arg Val Ser Glu Pro Val Asn His Phe Phe Phe
                295                 300                 305

CTC TTT GCT TTC CTA AAC CCG TGC TTC GAC CCA CTC ATA TAT GGG TAT       1014
Leu Phe Ala Phe Leu Asn Pro Cys Phe Asp Pro Leu Ile Tyr Gly Tyr
310                 315                 320

TTC TCT TTG TAGTTGGGAG ACTACACAAG AACTCAGATA GAAATAAGGT               1063
Phe Ser Leu
325

AACTAATTGC ACCAATTGAG AATAAACTCA AAGCTTTTGA CACACTTATA TACAAGGCAG     1123

GGTTTAAGGT TAGATTATCA ACCTTGTTTT TGTACAGAGT TTGTTGTTAG AGCTTCAGAA     1183

GACCTTCAAA AACAAAAAAA AAAAAAAAAA AAAAAAAAAA AAAA                     1227

(2) INFORMATION FOR SEQ ID NO:2:

(i) SEQUENCE CHARACTERISTICS:
        (A) LENGTH: 327 amino acids
        (B) TYPE: amino acid
        (D) TOPOLOGY: unknown (ii) MOLECULE TYPE: protein (xi) SEQUENCE DESCRIPTION: SEQ ID NO:2:

Met Ala Asn Asn Ala Ser Leu Glu Gln Asp Pro Asn His Cys Ser Ala
1               5                   10                  15

Ile Asn Asn Ser Ile Pro Leu Ile Gln Gly Lys Leu Pro Thr Leu Thr
                20                  25                  30

Val Ser Gly Lys Ile Arg Val Thr Val Thr Phe Phe Leu Phe Leu Leu
            35                  40                  45

Ser Thr Ala Phe Asn Ala Ser Phe Leu Leu Lys Leu Gln Lys Trp Thr
```

```
                50                    55                    60
Gln Lys Arg Lys Lys Gly Lys Lys Leu Ser Arg Met Lys Val Leu Leu
 65                  70                  75                  80

Lys His Leu Thr Leu Ala Asn Leu Leu Glu Thr Leu Ile Val Met Pro
                 85                  90                  95

Leu Asp Gly Met Trp Asn Ile Thr Val Gln Trp Tyr Ala Gly Glu Phe
                100                 105                 110

Leu Cys Lys Val Leu Ser Tyr Leu Lys Leu Phe Ser Met Tyr Ala Pro
                115                 120                 125

Ala Phe Met Met Val Val Ile Ser Leu Asp Arg Ser Leu Ala Ile Thr
                130                 135                 140

Gln Pro Leu Ala Val Gln Ser Asn Ser Lys Leu Glu Gln Ser Met Ile
145                 150                 155                 160

Ser Leu Ala Trp Ile Leu Ser Ile Val Phe Ala Gly Pro Gln Leu Tyr
                165                 170                 175

Ile Phe Arg Met Ile Tyr Leu Ala Asp Gly Ser Gly Pro Thr Val Phe
                180                 185                 190

Ser Gln Cys Val Thr His Cys Ser Phe Pro Gln Trp Trp His Gln Ala
                195                 200                 205

Phe Tyr Asn Phe Phe Thr Phe Gly Cys Leu Phe Ile Ile Pro Leu Leu
210                 215                 220

Ile Met Leu Ile Cys Asn Ala Lys Ile Ile Phe Ala Leu Thr Arg Val
225                 230                 235                 240

Leu His Gln Asp Pro Arg Lys Leu Gln Met Asn Gln Ser Lys Asn Asn
                245                 250                 255

Ile Pro Arg Ala Arg Leu Arg Thr Leu Lys Met Thr Val Ala Phe Ala
                260                 265                 270

Thr Ser Phe Val Val Cys Trp Thr Pro Tyr Tyr Val Leu Gly Ile Trp
                275                 280                 285

Tyr Trp Phe Asp Pro Glu Met Leu Asn Arg Val Ser Glu Pro Val Asn
                290                 295                 300

His Phe Phe Phe Leu Phe Ala Phe Leu Asn Pro Cys Phe Asp Pro Leu
305                 310                 315                 320

Ile Tyr Gly Tyr Phe Ser Leu
                325

(2) INFORMATION FOR SEQ ID NO:3:

(i) SEQUENCE CHARACTERISTICS:
        (A) LENGTH: 2160 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 25..1008

(xi) SEQUENCE DESCRIPTION: SEQ ID NO:3:

CGGAGCCTTG TGTCCTGGGA AAAT ATG GCA AAC AGT GCC TCT CCT GAA CAG        51
                         Met Ala Asn Ser Ala Ser Pro Glu Gln
                          1               5

AAT CAA AAT CAC TGT TCA GCC ATC AAC AAC AGC ATC CCA CTG ATG CAG       99
Asn Gln Asn His Cys Ser Ala Ile Asn Asn Ser Ile Pro Leu Met Gln
 10                  15                  20                  25

GGC AAC CTC CCC ACT CTG ACC TTG TCT GGA AAG ATC CGA GTG ACG GTT      147
Gly Asn Leu Pro Thr Leu Thr Leu Ser Gly Lys Ile Arg Val Thr Val
```

```
                              30                    35                    40
ACT TTC TTC CTT TTT CTG CTC TCT GCG ACC TTT AAT GCT TCT TTC TTG        195
Thr Phe Phe Leu Phe Leu Leu Ser Ala Thr Phe Asn Ala Ser Phe Leu
                45                    50                    55

TTG AAA CTT CAG AAG TGG ACA CAG AAG AAA GAG AAA GGG AAA AAG CTC        243
Leu Lys Leu Gln Lys Trp Thr Gln Lys Lys Glu Lys Gly Lys Lys Leu
                60                    65                    70

TCA AGA ATG AAG CTG CTC TTA AAA CAT CTG ACC TTA GCC AAC CTG TTG        291
Ser Arg Met Lys Leu Leu Leu Lys His Leu Thr Leu Ala Asn Leu Leu
        75                    80                    85

GAG ACT CTG ATT GTC ATG CCA CTG GAT GGG ATG TGG AAC ATT ACA GTC        339
Glu Thr Leu Ile Val Met Pro Leu Asp Gly Met Trp Asn Ile Thr Val
    90                    95                   100                   105

CAA TGG TAT GCT GGA GAG TTA CTC TGC AAA GTT CTC AGT TAT CTA AAG        387
Gln Trp Tyr Ala Gly Glu Leu Leu Cys Lys Val Leu Ser Tyr Leu Lys
                    110                   115                   120

CTT TTC TCC ATG TAT GCC CCA GCC TTC ATG ATG GTG GTG ATC AGC CTG        435
Leu Phe Ser Met Tyr Ala Pro Ala Phe Met Met Val Val Ile Ser Leu
                125                   130                   135

GAC CGC TCC CTG GCT ATC ACG AGG CCC CTA GCT TTG AAA AGC AAC AGC        483
Asp Arg Ser Leu Ala Ile Thr Arg Pro Leu Ala Leu Lys Ser Asn Ser
            140                   145                   150

AAA GTC GGA CAG TCC ATG GTT GGC CTG GCC TGG ATC CTC AGT AGT GTC        531
Lys Val Gly Gln Ser Met Val Gly Leu Ala Trp Ile Leu Ser Ser Val
    155                   160                   165

TTT GCA GGA CCA CAG TTA TAC ATC TTC AGG ATG ATT CAT CTA GCA GAC        579
Phe Ala Gly Pro Gln Leu Tyr Ile Phe Arg Met Ile His Leu Ala Asp
170                   175                   180                   185

AGC TCT GGA CAG ACA AAA GTT TTC TCT CAA TGT GTA ACA CAC TGC AGT        627
Ser Ser Gly Gln Thr Lys Val Phe Ser Gln Cys Val Thr His Cys Ser
                190                   195                   200

TTT TCA CAA TGG TGG CAT CAA GCA TTT TAT AAC TTT TTC ACC TTC AGC        675
Phe Ser Gln Trp Trp His Gln Ala Phe Tyr Asn Phe Phe Thr Phe Ser
            205                   210                   215

TGC CTC TTC ATC ATC CCT CTT TTC ATC ATG CTG ATC TGC AAT GCA AAA        723
Cys Leu Phe Ile Ile Pro Leu Phe Ile Met Leu Ile Cys Asn Ala Lys
        220                   225                   230

ATC ATC TTC ACC CTG ACA CGG GTC CTT CAT CAG GAC CCC CAC GAA CTA        771
Ile Ile Phe Thr Leu Thr Arg Val Leu His Gln Asp Pro His Glu Leu
    235                   240                   245

CAA CTG AAT CAG TCC AAG AAC AAT ATA CCA AGA GCA CGG CTG AAG ACT        819
Gln Leu Asn Gln Ser Lys Asn Asn Ile Pro Arg Ala Arg Leu Lys Thr
250                   255                   260                   265

CTA AAA ATG ACG GTT GCA TTT GCC ACT TCA TTT ACT GTC TGC TGG ACT        867
Leu Lys Met Thr Val Ala Phe Ala Thr Ser Phe Thr Val Cys Trp Thr
                270                   275                   280

CCC TAC TAT GTC CTA GGA ATT TGG TAT TGG TTT GAT CCT GAA ATG TTA        915
Pro Tyr Tyr Val Leu Gly Ile Trp Tyr Trp Phe Asp Pro Glu Met Leu
            285                   290                   295

AAC AGG TTG TCA GAC CCA GTA AAT CAC TTC TTC TTT CTC TTT GCC TTT        963
Asn Arg Leu Ser Asp Pro Val Asn His Phe Phe Phe Leu Phe Ala Phe
        300                   305                   310

TTA AAC CCA TGC TTT GAT CCA CTT ATC TAT GGA TAT TTT TCT CTG              1008
Leu Asn Pro Cys Phe Asp Pro Leu Ile Tyr Gly Tyr Phe Ser Leu
    315                   320                   325

TGATTGATAG ACTACACAAG AAGTCATATG AAGAAGGGTA AGGTAATGAA TCTCTCCATC        1068

TGGGAATGAT AACACAAAT GTTGGAGCAT GTTTACATAC AAACAAAGTA GGATTTACAC         1128

TTAAGTTATC ATTCTTTTAG AAACTCAGTC TTCAGAGCCT CAATTATTAA GGAAAAGTCT        1188
```

```
TCAGGAAAAA TACTAAAATA TTTTCTCTTC CTCATAAGCT TCTAAATTAA TCTCTGCCTT     1248

TTCTGACCTC ATATAACACA TTATGTAGGT TTCTTATCAC TTTCTCTTTG CATAATAATG     1308

TACTAATATT TAAATACCT TCAGCCTAAG GCACAAGGAT GCCAAAAAAA CAAAGGTGAG      1368
```

```
TCAGGAAAAA TACTAAAATA TTTTCTCTTC CTCATAAGCT TCTAAATTAA TCTCTGCCTT     1248

TTCTGACCTC ATATAACACA TTATGTAGGT TTCTTATCAC TTTCTCTTTG CATAATAATG     1308

TACTAATATT TAAATACCT  TCAGCCTAAG GCACAAGGAT GCCAAAAAAA CAAAGGTGAG     1368

AACCCACAAC ACAGGTCTAA ACTCAGCATG CTTGGTGAGT TTTTCTCCAA AGGGGCATAT     1428

TAGCAATTAG AGTTGTATGC TATATAATAC ATAGAGCACA GAGCCCTTTG CCCATAATAT     1488

CAACTTTCCC TCCTATAGTT AAAAGAAAA  AAAAATGAAT CTATTTTTCT CTTTGGCTTC     1548

AAAAGCATTC TGACATTTGG AGGAGTCAGT AACCAATCCC ACCAACCACT CCAGCAACCT     1608

GACAAGACTA TGAGTAGTTC TCCTTCATCC TATTTATGTG GTACAGGTTG TGAAGTATCT     1668

CTATATAAAG GGAAATTTTA GAGGGGTTAG GATTTGGACA GGGGTTTAGA ACATTCCTCT     1728

AAGCTATCTA GTCTGTGGAG TTTGTGGCAA TTAATTGCCA TAAAATAACA TGTTTCCAAA     1788

TGCAACTAAG AAAATACTCA TAGTGAGTAC GCTCTATGCA TAGTATGACT TCTATTTAAT     1848

GTGAAGAATT TTTTGTCTCT CTCCTGATCT TACTAAATCC ATATTTCATA AATGAACTGA     1908

GAATAATTAA CAAAATTAAG CAAATGCACA AGCAAAAGAT GCTTGATACA CAAAAGGAAC     1968

TCTGGAGAGA AAACTACAGC TTCAGTCTGT ACAGATCAAA GAAGACAGAA CATGTCAGGG     2028

GAAGGAGGAA AGATCTTGAT GCAGGGTTTC TTAACCTGCA GTCTATGCAC AACACTATAT     2088

TTCCATGTAA TGTTTTTATT TCAGCCCTAT TTGTATTATT TTGTGCATTT AAAAAACACA    2148

ATCTTAAGGC CG                                                         2160

(2) INFORMATION FOR SEQ ID NO:4:

(i) SEQUENCE CHARACTERISTICS:
        (A) LENGTH: 328 amino acids
        (B) TYPE: amino acid
        (D) TOPOLOGY: unknown (ii) MOLECULE TYPE: protein (xi) SEQUENCE DESCRIPTION: SEQ ID NO:4:

Met Ala Asn Ser Ala Ser Pro Glu Gln Asn Gln Asn His Cys Ser Ala
 1               5                  10                  15

Ile Asn Asn Ser Ile Pro Leu Met Gln Gly Asn Leu Pro Thr Leu Thr
                20                  25                  30

Leu Ser Gly Lys Ile Arg Val Thr Val Thr Phe Phe Leu Phe Leu Leu
            35                  40                  45

Ser Ala Thr Phe Asn Ala Ser Phe Leu Leu Lys Leu Gln Lys Trp Thr
        50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Leu
               100                 105                 110

Leu Cys Lys Val Leu Ser Tyr Leu Lys Leu Phe Ser Met Tyr Ala Pro
           115                 120                 125

Ala Phe Met Met Val Val Ile Ser Leu Asp Arg Ser Leu Ala Ile Thr
       130                 135                 140

Arg Pro Leu Ala Leu Lys Ser Asn Ser Lys Val Gly Gln Ser Met Val
145                 150                 155                 160

Gly Leu Ala Trp Ile Leu Ser Ser Val Phe Ala Gly Pro Gln Leu Tyr
               165                 170                 175

Ile Phe Arg Met Ile His Leu Ala Asp Ser Ser Gly Gln Thr Lys Val
```

-continued

```
                180                 185                 190
Phe Ser Gln Cys Val Thr His Cys Ser Phe Ser Gln Trp Trp His Gln
            195                 200                 205
Ala Phe Tyr Asn Phe Phe Thr Phe Ser Cys Leu Phe Ile Ile Pro Leu
210                 215                 220
Phe Ile Met Leu Ile Cys Asn Ala Lys Ile Ile Phe Thr Leu Thr Arg
225                 230                 235                 240
Val Leu His Gln Asp Pro His Glu Leu Gln Leu Asn Gln Ser Lys Asn
            245                 250                 255
Asn Ile Pro Arg Ala Arg Leu Lys Thr Leu Lys Met Thr Val Ala Phe
            260                 265                 270
Ala Thr Ser Phe Thr Val Cys Trp Thr Pro Tyr Tyr Val Leu Gly Ile
            275                 280                 285
Trp Tyr Trp Phe Asp Pro Glu Met Leu Asn Arg Leu Ser Asp Pro Val
            290                 295                 300
Asn His Phe Phe Phe Leu Phe Ala Phe Leu Asn Pro Cys Phe Asp Pro
305                 310                 315                 320
Leu Ile Tyr Gly Tyr Phe Ser Leu
                325
```

(2) INFORMATION FOR SEQ ID NO:5:

(i) SEQUENCE CHARACTERISTICS:
        (A) LENGTH: 355 amino acids
        (B) TYPE: amino acid
        (D) TOPOLOGY: unknown (ii) MOLECULE TYPE: protein (xi) SEQUENCE DESCRIPTION: SEQ ID NO:5:

```
Met Glu Ser Asp Ser Phe Glu Asp Phe Trp Lys Gly Glu Asp Leu Ser
1               5                   10                  15
Asn Tyr Ser Tyr Ser Ser Thr Leu Pro Pro Phe Leu Leu Asp Ala Ala
            20                  25                  30
Pro Cys Glu Pro Glu Ser Leu Glu Ile Asn Lys Tyr Phe Val Val Ile
            35                  40                  45
Ile Tyr Ala Leu Val Phe Leu Leu Ser Leu Leu Gly Asn Ser Leu Val
50                  55                  60
Met Leu Val Ile Leu Tyr Ser Arg Val Gly Arg Ser Val Thr Asp Val
65                  70                  75                  80
Tyr Leu Leu Asn Leu Ala Leu Ala Asp Leu Leu Phe Ala Leu Thr Leu
            85                  90                  95
Pro Ile Trp Ala Ala Ser Lys Val Asn Gly Trp Ile Phe Gly Thr Phe
            100                 105                 110
Leu Cys Lys Val Val Ser Leu Leu Lys Glu Val Asn Phe Tyr Ser Gly
            115                 120                 125
Ile Leu Leu Leu Ala Cys Ile Ser Val Asp Arg Tyr Leu Ala Ile Val
            130                 135                 140
His Ala Thr Arg Thr Leu Thr Gln Lys Arg Tyr Leu Val Lys Phe Ile
145                 150                 155                 160
Cys Leu Ser Ile Trp Gly Leu Ser Leu Leu Ala Leu Pro Val Leu
            165                 170                 175
Leu Phe Arg Arg Thr Val Tyr Ser Ser Asn Val Ser Pro Ala Cys Tyr
            180                 185                 190
Glu Asp Met Gly Asn Asn Thr Ala Asn Trp Arg Met Leu Leu Arg Ile
            195                 200                 205
```

```
Leu Pro Gln Ser Phe Gly Phe Ile Val Pro Leu Leu Ile Met Leu Phe
    210                 215                 220
Cys Tyr Gly Phe Thr Leu Arg Thr Leu Phe Lys Ala His Met Gly Gln
225                 230                 235                 240
Lys His Arg Ala Met Arg Val Ile Phe Ala Val Val Leu Ile Phe Leu
                245                 250                 255
Leu Cys Trp Leu Pro Tyr Asn Leu Val Leu Leu Ala Asp Thr Leu Met
            260                 265                 270
Arg Thr Gln Val Ile Gln Glu Thr Cys Glu Arg Arg Asn His Ile Asp
        275                 280                 285
Arg Ala Leu Asp Ala Thr Glu Ile Leu Gly Ile Leu His Ser Cys Leu
    290                 295                 300
Asn Pro Leu Ile Tyr Ala Phe Ile Gly Gln Lys Phe Arg His Gly Leu
305                 310                 315                 320
Leu Lys Ile Leu Ala Ile His Gly Leu Ile Ser Lys Asp Ser Leu Pro
                325                 330                 335
Lys Asp Ser Arg Pro Ser Phe Val Gly Ser Ser Ser Gly His Thr Ser
            340                 345                 350
Thr Thr Leu
    355

(2) INFORMATION FOR SEQ ID NO:6:

(i) SEQUENCE CHARACTERISTICS:
        (A) LENGTH: 407 amino acids
        (B) TYPE: amino acid
        (D) TOPOLOGY: unknown (ii) MOLECULE TYPE: protein (xi) SEQUENCE DESCRIPTION: SEQ ID NO:6:

Met Asp Asn Val Leu Pro Met Asp Ser Asp Leu Phe Pro Asn Ile Ser
1               5                   10                  15
Thr Asn Thr Ser Glu Ser Asn Gln Phe Val Gln Pro Thr Trp Gln Ile
                20                  25                  30
Val Leu Trp Ala Ala Ala Tyr Thr Val Ile Val Val Thr Ser Val Val
            35                  40                  45
Gly Asn Val Val Val Ile Trp Ile Ile Leu Ala His Lys Arg Met Arg
50                  55                  60
Thr Val Thr Asn Tyr Phe Leu Val Asp Leu Ala Phe Ala Glu Ala Cys
65                  70                  75                  80
Met Ala Ala Phe Asn Thr Val Val Asn Phe Thr Tyr Ala Val His Asn
                85                  90                  95
Val Trp Tyr Tyr Gly Leu Phe Tyr Cys Lys Phe His Asn Phe Phe Pro
            100                 105                 110
Ile Ala Ala Leu Phe Ala Ser Ile Tyr Ser Met Thr Ala Val Ala Phe
        115                 120                 125
Asp Arg Tyr Met Ala Ile Ile His Pro Leu Gln Pro Arg Leu Ser Ala
    130                 135                 140
Thr Ala Thr Lys Val Val Ile Phe Val Ile Trp Val Leu Ala Leu Leu
145                 150                 155                 160
Leu Ala Phe Pro Gln Gly Tyr Tyr Ser Thr Thr Glu Thr Met Pro Ser
                165                 170                 175
Arg Val Val Cys Met Ile Glu Trp Pro Glu His Pro Asn Arg Thr Tyr
            180                 185                 190
Glu Lys Ala Tyr His Ile Cys Val Thr Val Leu Ile Tyr Phe Leu Pro
        195                 200                 205
```

-continued

```
Leu Leu Val Ile Gly Tyr Ala Tyr Thr Val Val Gly Ile Thr Leu Trp
    210                 215                 220
Ala Ser Glu Ile Pro Gly Asp Ser Ser Asp Arg Tyr His Glu Gln Val
225                 230                 235                 240
Ser Ala Lys Arg Lys Val Val Lys Met Met Ile Val Val Val Cys Thr
                245                 250                 255
Phe Ala Ile Cys Trp Leu Pro Phe His Val Phe Phe Leu Leu Pro Tyr
            260                 265                 270
Ile Asn Pro Asp Leu Tyr Leu Lys Lys Phe Ile Gln Gln Val Tyr Leu
        275                 280                 285
Ala Ser Met Trp Leu Ala Met Ser Ser Thr Met Tyr Asn Pro Ile Ile
    290                 295                 300
Tyr Cys Cys Leu Asn Asp Arg Phe Arg Leu Gly Phe Lys His Ala Phe
305                 310                 315                 320
Arg Cys Cys Pro Phe Ile Ser Ala Gly Asp Tyr Glu Gly Leu Glu Met
                325                 330                 335
Lys Ser Thr Arg Tyr Leu Gln Thr Gln Ser Ser Val Tyr Lys Val Ser
            340                 345                 350
Arg Leu Glu Thr Thr Ile Ser Thr Val Val Gly Ala His Glu Glu Glu
        355                 360                 365
Pro Glu Glu Gly Pro Lys Ala Thr Pro Ser Ser Leu Asp Leu Thr Ser
    370                 375                 380
Asn Gly Ser Ser Arg Ser Asn Ser Lys Thr Met Thr Glu Ser Ser Ser
385                 390                 395                 400
Phe Tyr Ser Asn Met Leu Ala
                405

(2) INFORMATION FOR SEQ ID NO:7:

(i) SEQUENCE CHARACTERISTICS:
        (A) LENGTH: 468 amino acids
        (B) TYPE: amino acid
        (D) TOPOLOGY: unknown (ii) MOLECULE TYPE: protein (xi) SEQUENCE DESCRIPTION: SEQ ID NO:7:

Ala Ser Glu Pro Gly Asn Leu Ser Ser Ala Ala Pro Leu Pro Asp Gly
1               5                   10                  15
Ala Ala Thr Ala Ala Arg Leu Leu Val Pro Ala Ser Pro Pro Ala Ser
            20                  25                  30
Leu Leu Pro Pro Ala Ser Glu Ser Pro Glu Pro Leu Ser Gln Gln Trp
        35                  40                  45
Thr Ala Gly Met Gly Leu Leu Met Ala Leu Ile Val Leu Leu Ile Val
    50                  55                  60
Ala Gly Asn Val Leu Val Ile Val Ala Ile Ala Lys Thr Pro Arg Leu
65                  70                  75                  80
Gln Thr Leu Thr Asn Leu Phe Ile Met Ser Leu Ala Ser Ala Asp Leu
                85                  90                  95
Val Met Gly Leu Leu Val Val Pro Phe Gly Ala Thr Ile Val Val Trp
            100                 105                 110
Gly Arg Trp Glu Tyr Gly Ser Phe Phe Cys Glu Leu Trp Thr Ser Val
        115                 120                 125
Asp Val Leu Cys Val Thr Ala Ser Ile Glu Thr Leu Cys Val Ile Ala
    130                 135                 140
Leu Asp Arg Tyr Leu Ala Ile Thr Ser Pro Phe Arg Tyr Gln Ser Leu
```

-continued

```
            145                 150                 155                 160
Leu Thr Arg Ala Arg Ala Arg Gly Leu Val Cys Thr Val Trp Ala Ile
                165                 170                 175
Ser Ala Leu Val Ser Phe Leu Pro Ile Leu Met His Trp Trp Arg Ala
                180                 185                 190
Glu Ser Asp Glu Ala Arg Arg Cys Tyr Asn Asp Pro Lys Cys Cys Asp
            195                 200                 205
Phe Val Thr Asn Arg Ala Tyr Ala Ile Ala Ser Ser Val Val Ser Phe
            210                 215                 220
Tyr Val Pro Leu Cys Ile Met Ala Phe Val Tyr Leu Arg Val Phe Arg
225                 230                 235                 240
Glu Ala Gln Lys Gln Val Lys Lys Ile Asp Ser Cys Glu Arg Arg Phe
                245                 250                 255
Leu Gly Gly Pro Ala Arg Pro Pro Ser Pro Ser Pro Ser Pro Val Pro
                260                 265                 270
Ala Pro Ala Pro Pro Gly Pro Arg Pro Ala Ala Ala Ala
                275                 280                 285
Thr Ala Pro Leu Ala Asn Gly Arg Ala Gly Lys Arg Arg Pro Ser Arg
                290                 295                 300
Leu Val Ala Leu Arg Glu Gln Lys Ala Leu Lys Thr Leu Gly Ile Ile
305                 310                 315                 320
Met Gly Val Phe Thr Leu Cys Trp Leu Pro Phe Phe Leu Ala Asn Val
                325                 330                 335
Val Lys Ala Phe His Arg Glu Leu Val Pro Asp Arg Leu Phe Val Phe
                340                 345                 350
Phe Asn Trp Leu Gly Tyr Ala Asn Ser Ala Phe Asn Pro Ile Ile Tyr
                355                 360                 365
Cys Arg Ser Pro Asp Phe Arg Lys Ala Phe Gln Gly Leu Leu Cys Cys
370                 375                 380
Ala Arg Arg Ala Ala Arg Arg His Ala Thr His Gly Asp Arg Pro
385                 390                 395                 400
Arg Ala Ser Gly Cys Leu Ala Arg Pro Gly Pro Pro Ser Pro Gly
                405                 410                 415
Ala Ala Ser Asp Asp Asp Asp Asp Val Val Gly Ala Thr Pro Pro
                420                 425                 430
Ala Arg Leu Leu Glu Pro Trp Ala Gly Cys Asn Gly Gly Ala Ala Ala
                435                 440                 445
Asp Ser Asp Ser Ser Leu Asp Glu Pro Cys Arg Pro Gly Phe Ala Ser
                450                 455                 460
Glu Ser Lys Val
465
```

(2) INFORMATION FOR SEQ ID NO:8:

(i) SEQUENCE CHARACTERISTICS:
        (A) LENGTH: 348 amino acids
        (B) TYPE: amino acid
        (D) TOPOLOGY: unknown (ii) MOLECULE TYPE: protein (xi) SEQUENCE DESCRIPTION: SEQ ID NO:8:

```
Met Asn Gly Thr Glu Gly Pro Asn Phe Tyr Val Pro Phe Ser Asn Ala
1                   5                   10                  15
Thr Gly Val Val Arg Ser Pro Phe Glu Tyr Pro Gln Tyr Tyr Leu Ala
                20                  25                  30
```

-continued

```
Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
        50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
            195                 200                 205

Val Val His Phe Thr Ile Pro Met Ile Ile Ile Phe Phe Cys Tyr Gly
    210                 215                 220

Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
            245                 250                 255

Met Val Ile Ala Phe Leu Ile Cys Trp Val Pro Tyr Ala Ser Val Ala
            260                 265                 270

Phe Tyr Ile Phe Thr His Gln Gly Ser Asn Phe Gly Pro Ile Phe Met
        275                 280                 285

Thr Ile Pro Ala Phe Phe Ala Lys Ser Ala Ala Ile Tyr Asn Pro Val
    290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
            325                 330                 335

Val Ser Lys Thr Glu Thr Ser Gln Val Ala Pro Ala
            340                 345
```

CLONING AND EXPRESSION OF GONADOTROPIN-RELEASING HORMONE RECEPTOR

The present application is a continuation-in-part of co-pending application Ser. No. 08/080,386 filed Jun. 21, 1993, now U.S. Pat. No. 5,750,366, which is a continuation-in-part of application Ser. No. 07/904,072, filed Jun. 23, 1992, abandoned. The continuation-in-part applications are incorporated by reference herein in their entirety.

This invention was made, in part, with government support under 91-06877 awarded by the NSF. The government has certain rights in the invention.

1. INTRODUCTION

The present invention relates to the cloning of gonadotropin-releasing hormone receptor (GnRH-R), and genetically engineered host cells which express the GnRH-R. Such engineered cells may be used to evaluate and screen drugs and analogs of GnRH involved in GnRH-R activation, regulation and uncoupling.

2. BACKGROUND OF THE INVENTION

The GnRH-R is a key mediator in the integration of the neural and endocrine systems. Normal reproduction depends on the pulsatile release of physiological concentrations of GnRH which binds to specific high affinity pituitary receptors and triggers the secretion of the gonadotropins luteinizing hormone (LH) and follicle stimulating hormone (FSH). Whereas physiological concentrations of GnRH orchestrate normal reproduction, high levels of agonist lead to an opposite response, the suppression of gonadotropin secretion. The capacity of GnRH analogues both to activate and to inhibit the hypothalamic-pituitary-gonadal axis has led to their wide clinical utility in the treatment of a variety of disorders ranging from infertility to prostatic carcinoma.

The responsiveness and capacity of the gonadotrope GnRH-R is influenced by agonist, concentration and pattern of exposure (Clayton, 1989, J Endocrinol 120: 11–19). Both in vivo and in vitro studies have demonstrated that low concentration pulsatile GnRH is trophic to the receptor and that a high concentration of agonist induces receptor down-regulation and desensitization. The binding of GnRH to its receptor stimulates phospholipase C and generates inositol-1,4,5-triphosphate and diacylglycerol (Huckle & Conn, 1988, Endocrine Reviews 9: 387–395). These second messengers, in turn, release calcium from intracellular stores and activate protein kinase C. Receptor up-regulation appears to involve both protein kinase C and calcium (Huckle & Conn, 1988, Endocrine Reviews 9: 387–395; Huckle et al., 1988, Journal of Biological Chemistry 263: 3296–3302; Young et al., 1985, Journal of Endocrinology 107: 49–56). It is not certain which effectors underlie down-regulation.

While great progress has been made in understanding the mechanisms underlying GnRH-R regulation and desensitization through receptor is binding studies, direct measurement of GnRH-R gene transcription and biosynthesis has not been possible. Cloning of the GnRH-R cDNA would advance the evaluation of GnRH-R activation, regulation and uncoupling. Determining the primary sequence of the receptor would facilitate the directed design of improved analogues. However, despite intensive interest, heretofore, the GnRH-R gene has not been cloned and expressed in any species.

3. SUMMARY OF THE INVENTION

The present invention relates to the GnRH-R genes and proteins. The DNA sequences disclosed herein may be engineered into expression systems designed for the production of GnRH-R and/or cell lines which express the GnRH-R and preferably respond to GnRH induced signal transduction. Such cell lines may advantageously be used for screening and identifying GnRH agonists and antagonists. In accordance with another aspect of the invention, the GnRH DNA, antisense oligonucleotide sequences, the GnRH expression products, and antibodies to such products may be used in the diagnosis and therapy of reproductive disorders associated with abnormal expression of the GnRH-R; e.g., overexpression, underexpression or expression of a dysfunctional mutant receptor. Transgenic animals containing the GnRH-R transgene may be used as animal models for the evaluation of GnRH analogs in vivo.

The elucidation of the GnRH-R sequence described herein reflects a major advance in reproductive endocrinology and reveals the complex nature of GnRH-R signal transduction and regulation. Unlike most hormonal signals, GnRH is released in a pulsatile fashion, with the frequency and amplitude of the pulses conveying crucial information (Weiss et al., 1990, Mol. Endocrinol. 4: 557–564; Hasenleder et al., is 1991, Endocrinology 128: 509–517). GnRH-R binding capacity itself is either up- or down-regulated by agonists depending on duration of exposure and concentration (Loumaye & Catt, 1982, Science 215: 983–985). The clinical utility of GnRH agonists, which help control a variety of human diseases, including prostatic hypertrophy, prostatic cancer, endometriosis and precocious puberty, depends on this induction of pituitary desensitization. The cloning of the GnRH-R will lead to greater understanding of the complex interplay of hypothalamic, pituitary and gonadal hormones which underlies both pharmacotherapy and reproduction.

4. DESCRIPTION OF THE FIGURES

Figure 1B:
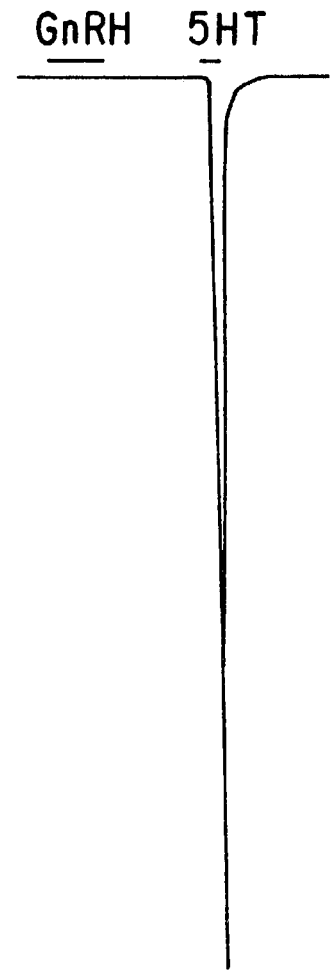

FIGS. 1A–B. Hybrid-arrest of serotonin (5HT) receptor and GnRH-R expression by antisense oligonucleotides. 100 nM 5HT or 200 nM GnRH were introduced into the bath at the horizontal lines. A, Response to 5HT and GnRH in oocytes previously injected with a mixture of rat brain RNA (for the 5HT response), αT3-1 RNA (for the GnRH response) and antisense $5HT_{1c}$ receptor oligonucleotide. 16 cells showed identical responses. B, Response to GnRH and 5HT in oocytes previously injected with a mixture of rat brain RNA, αT3-1 RNA and antisense WZ7 oligonucleotide. 24 cells had identical responses.

Figure 2A:
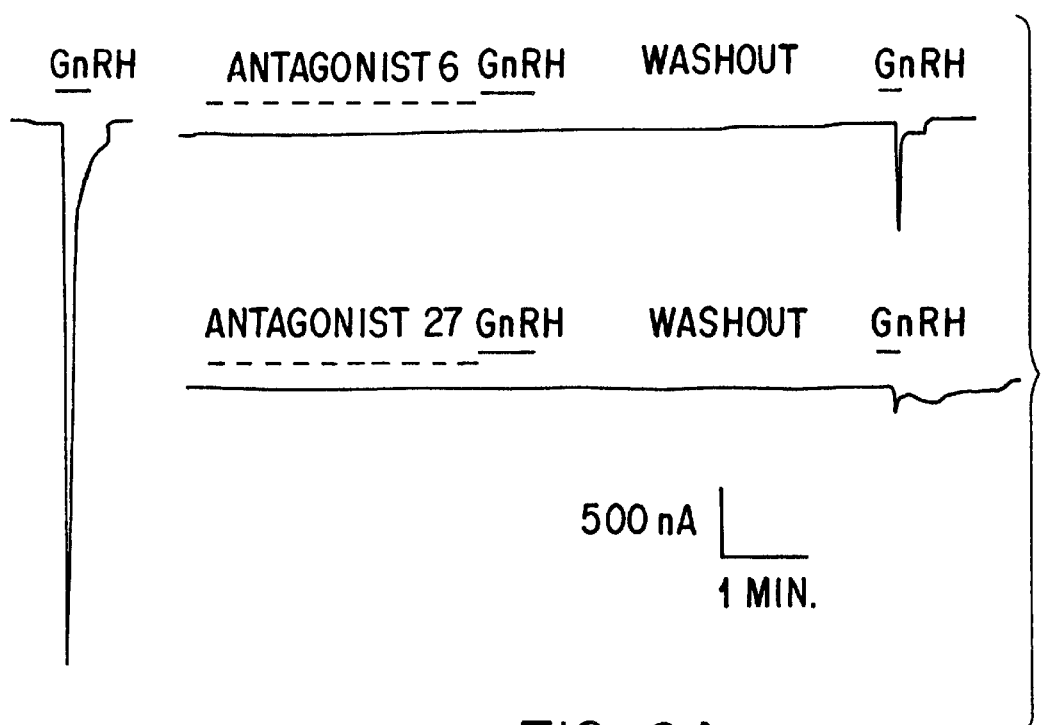
Figure 2B:
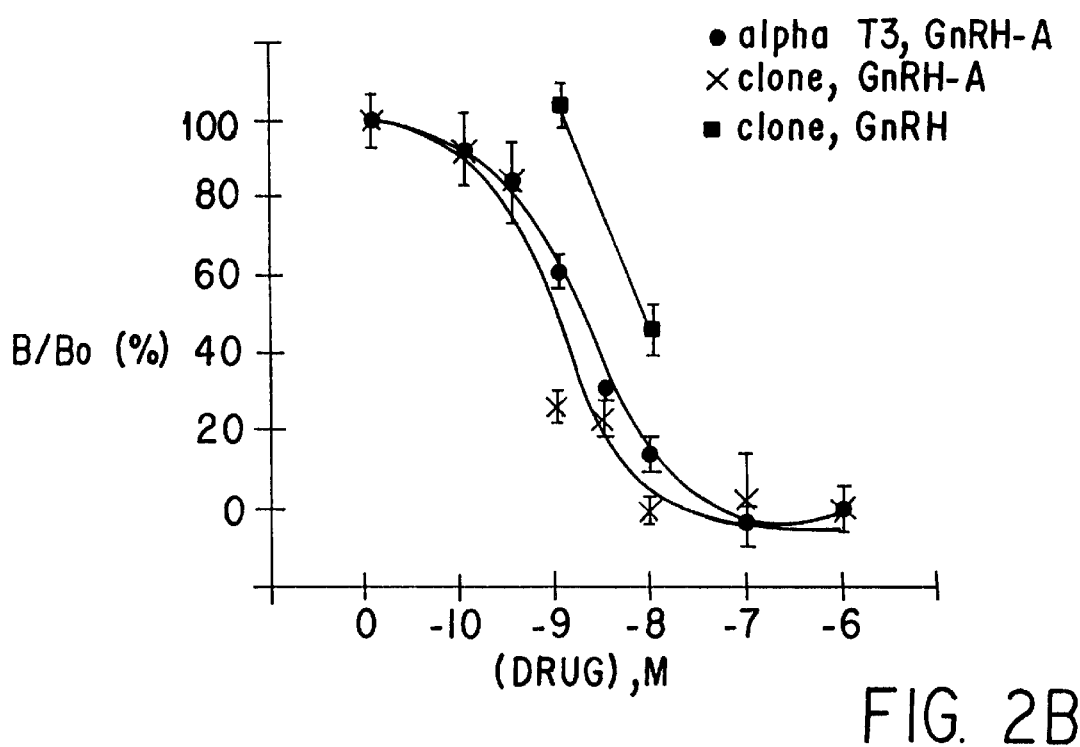

FIGS. 2A–B. Characterization of clone WZ25 expressed in oocytes. A, Electrophysiological response to GnRH of oocytes injected with the WZ25 transcript in the absence (left) or presence (right) of GnRH antagonist. The three tracings shown are from different cells. Solid and dotted lines indicate GnRH and GnRH antagonist administration, respectively. Uninjected oocytes had no response to GnRH (n=12). B, Displacement of $^{125}$I-GnRH-A by GnRH-A and GnRH in membranes of oocytes injected with transcript from is WZ25. A comparative displacement curve using αT3-1 cell membranes combined with membranes from uninjected oocytes is also shown (●). Error bars show SEM.

FIGS. 3A–B. Nucleotide (SEQ. ID NO: 1) and deduced amino acid sequences (SEQ. ID NO: 2) of clone WZ25. Numbering begins with the first methionine of the 981 base pair open reading frame. The deduced amino acid sequence is shown below the nucleotide sequence. Putative transmembrane regions I-VII are underlined. Symbols below the amino acid sequences indicate potential N-glycosylation sites (▲), and phosphorylation sites for protein kinase A (♦), Casein kinase 2 (●) and protein kinase C (*)) (Hubbard & Ivatt, 1981, Ann Rev. Biochem. 50: 555–583; Kemp & Pearson, 1990, Trends Biochem. Sci. 15: 342–346; Pearson & Kemp, 1991, Meth. Enzymol. 200: 62–81; Kennelly & Krebs, 1991, J. Biol. Chem. 266: 15555–15558).

Figure 4A:
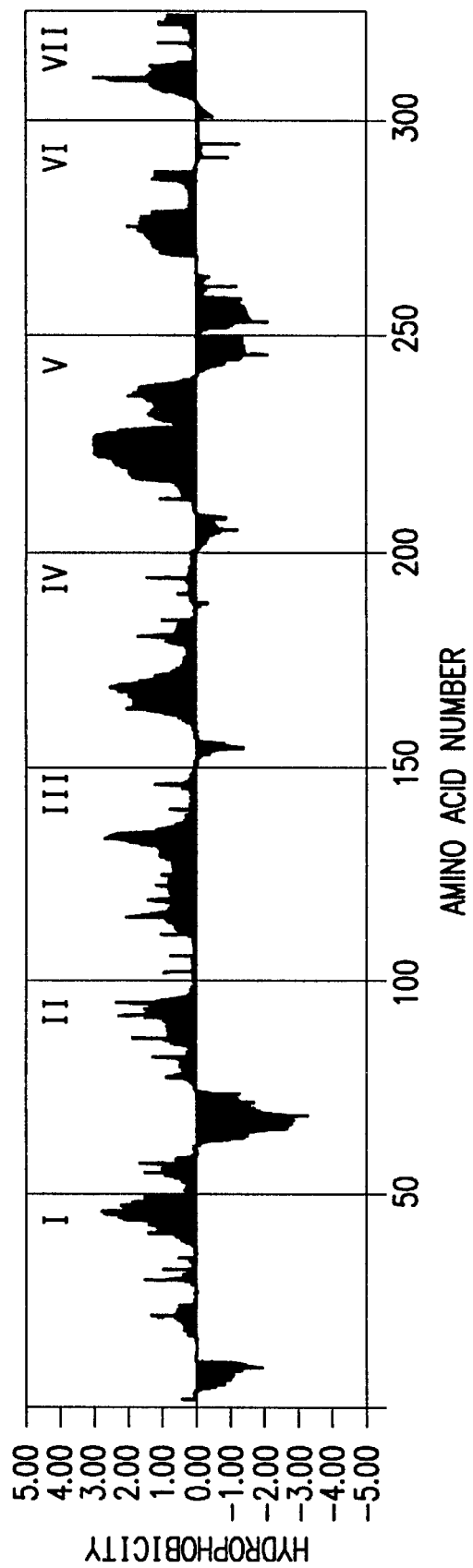

FIGS. 4A–4C. Hydrophobicity plot of the GnRH-R and amino acid sequence alignment of: GnRH, mouse gonadotropin-releasing hormone receptor (SEQ ID NO: 2), ILR, human interleukin-8 receptor (SEQ ID NO: 5) (Murphy & Tiffany, 1991, Science 253: 1280–1283); SPR, rat substance P receptor (SEQ ID NO: 6) (Hershey & Krause, 1990, Science 247: 958–962); β1R, human β1-adrenergic (SEQ ID NO: 7) (Frielle et al., 1987, Proc. Natl. Acad. Sci. USA 84: 7920–7924); and RHO, human rhodopsin (SEQ ID NO: 8) (Nathans & Hogness, 1984, Proc. Natl. Acad. Sci. USA 81: 4851–4855). I-VII denote putative regions. Boxes indicate identical amino acid residues.

FIGS. 5A, 5B, 5C, 5D, 5E, 5F. Distribution of GnRH-R mRNA.

FIG. 5A. Autoradiogram of solution hybridization assay using 2 μg of total mouse pituitary, GT-1, GH3 and AtT20 RNA and 625 ng of αT3-1 total RNA.

FIG. 5B. Northern blot analysis with 3μ of poly (A)+ αT3-1 RNA.

FIG. 5C. Antisense probe x-ray film autoradiography.

FIG. 5D. Sense probe control (calibration bar=50 μm)

FIG. 5F. Bright-field (calibration bar=100 μm) photomicrographs of emulsion-dipped anterior pituitary section. The molecular weight markers are Hind III digested λ DNA FIG. 6. Expression of the human GnRH-R cDNA in Xenopus oocytes FIG. 7. Displacement of [$^{125}$I]GnRH binding by GnRH-A, GnRH and antagonist 5 to membranes prepared from COS-1 cells transfected with the pSV2A-human GnRH-R construct.

Figure 8:
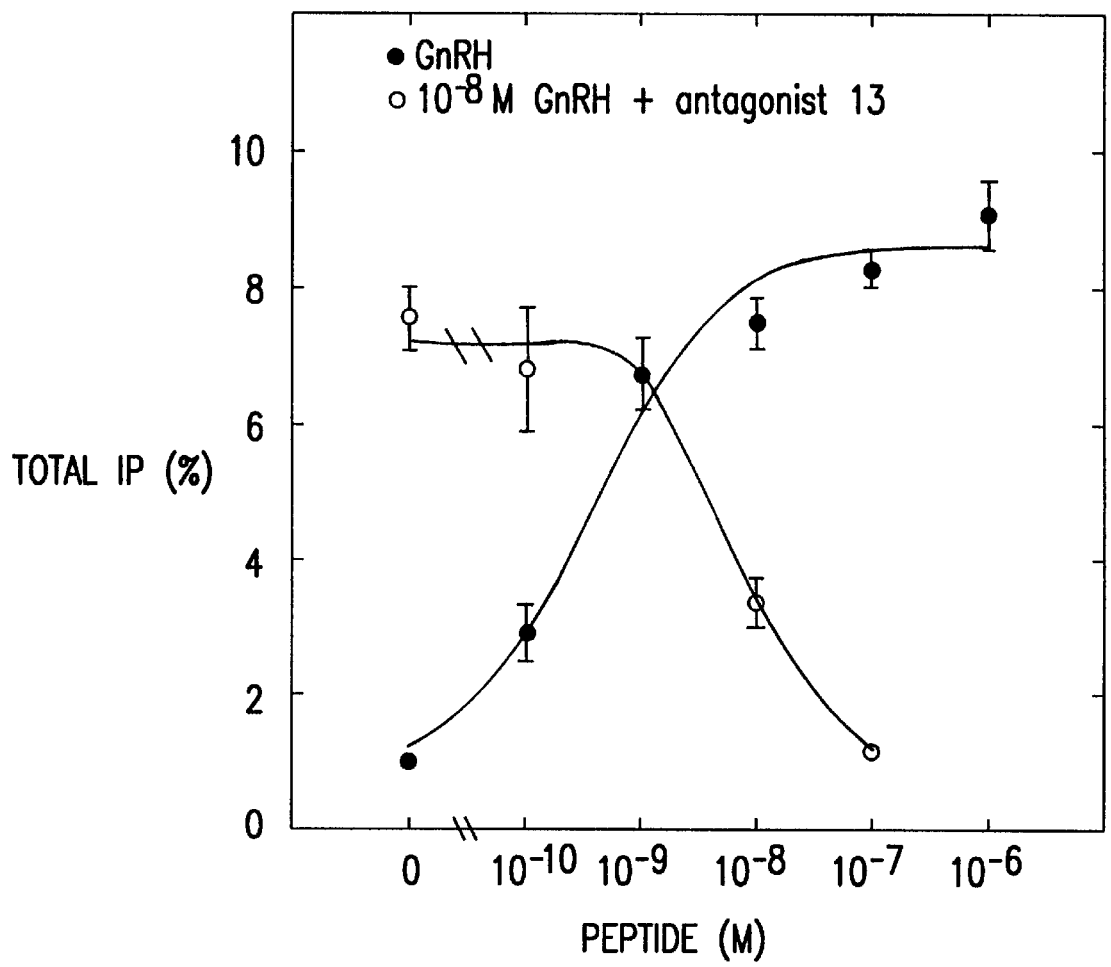

FIG. 8. Effects of GnRH and GnRH antagonist on inositol phosphate production in COS-1 cells transfected with pSV2A-human GnRH-R.

FIGS. 9A–9B. Nucleotide sequence (SEQ ID NO: 3) and putative amino acid sequence (SEQ ID NO: 4) of the human GnRH-R.

Figure 10:
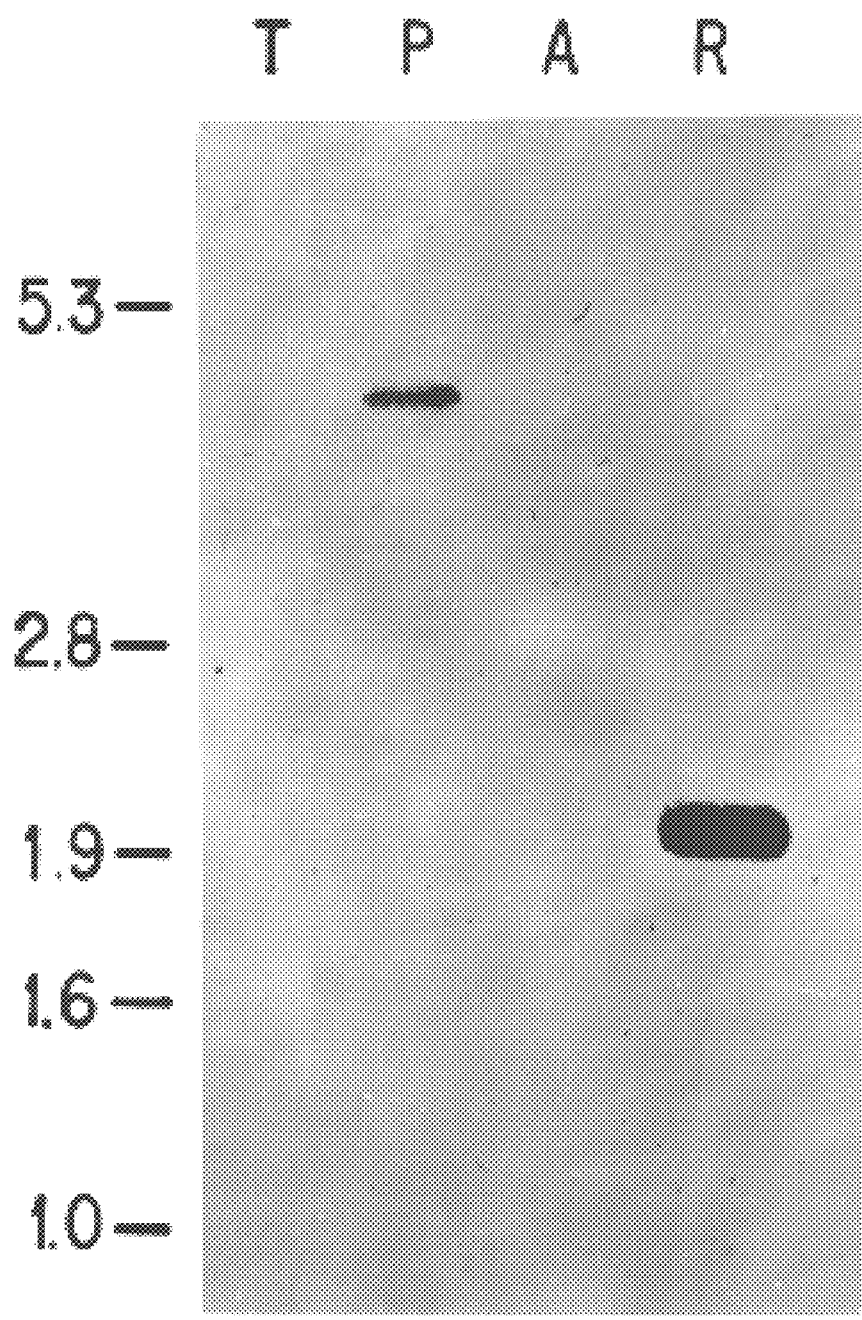

FIG. 10. Northern blot analysis with human GnRH-R cDNA: lane 1(T): human testis poly(A) RNA; lane 2 (P): human pituitary poly(A) RNA; lane 3 (A): human β-actin cDNA; lane 4(R): human GnRH-R cDNA.

Figure 11A:
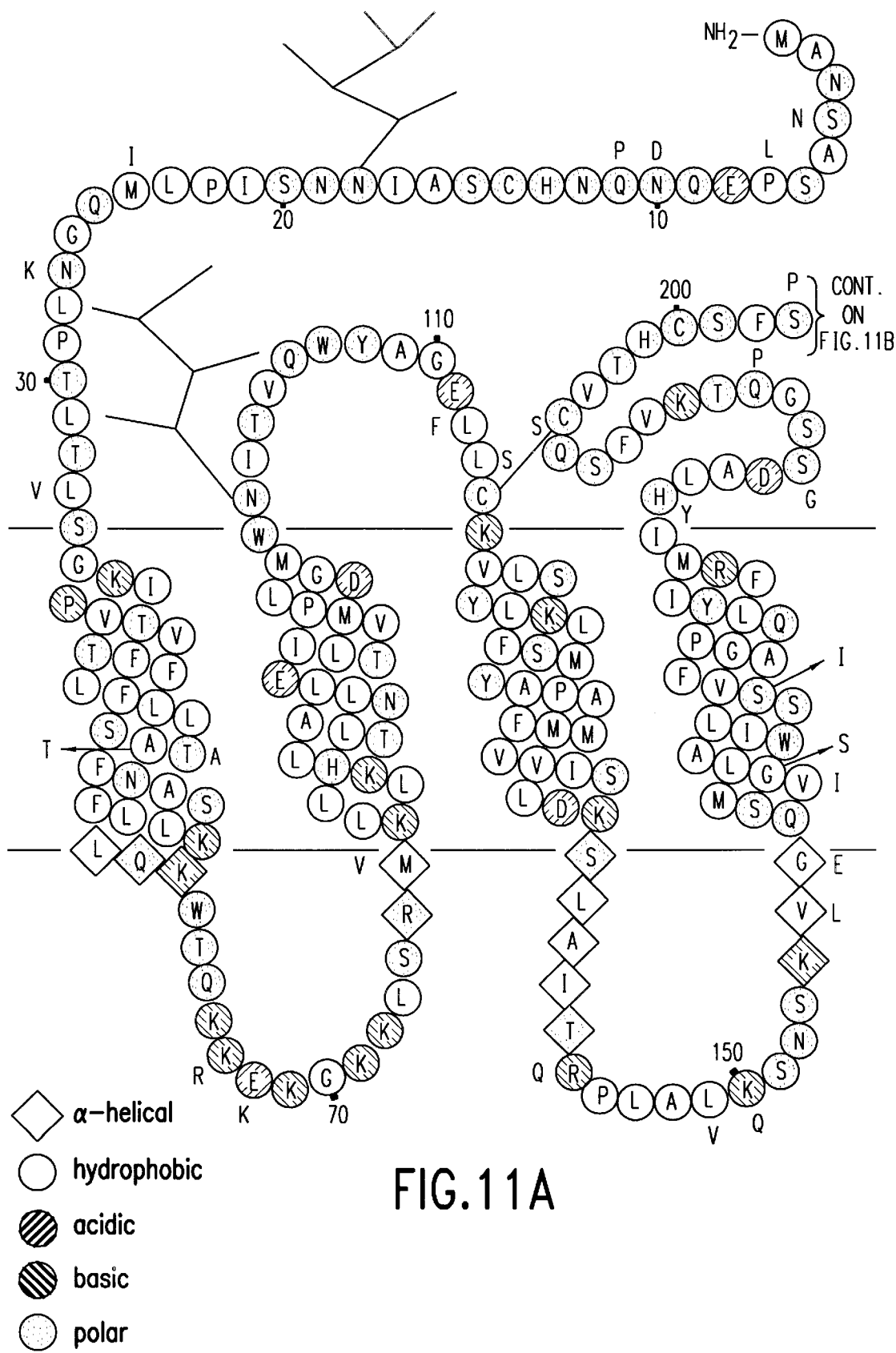
Figure 11B:
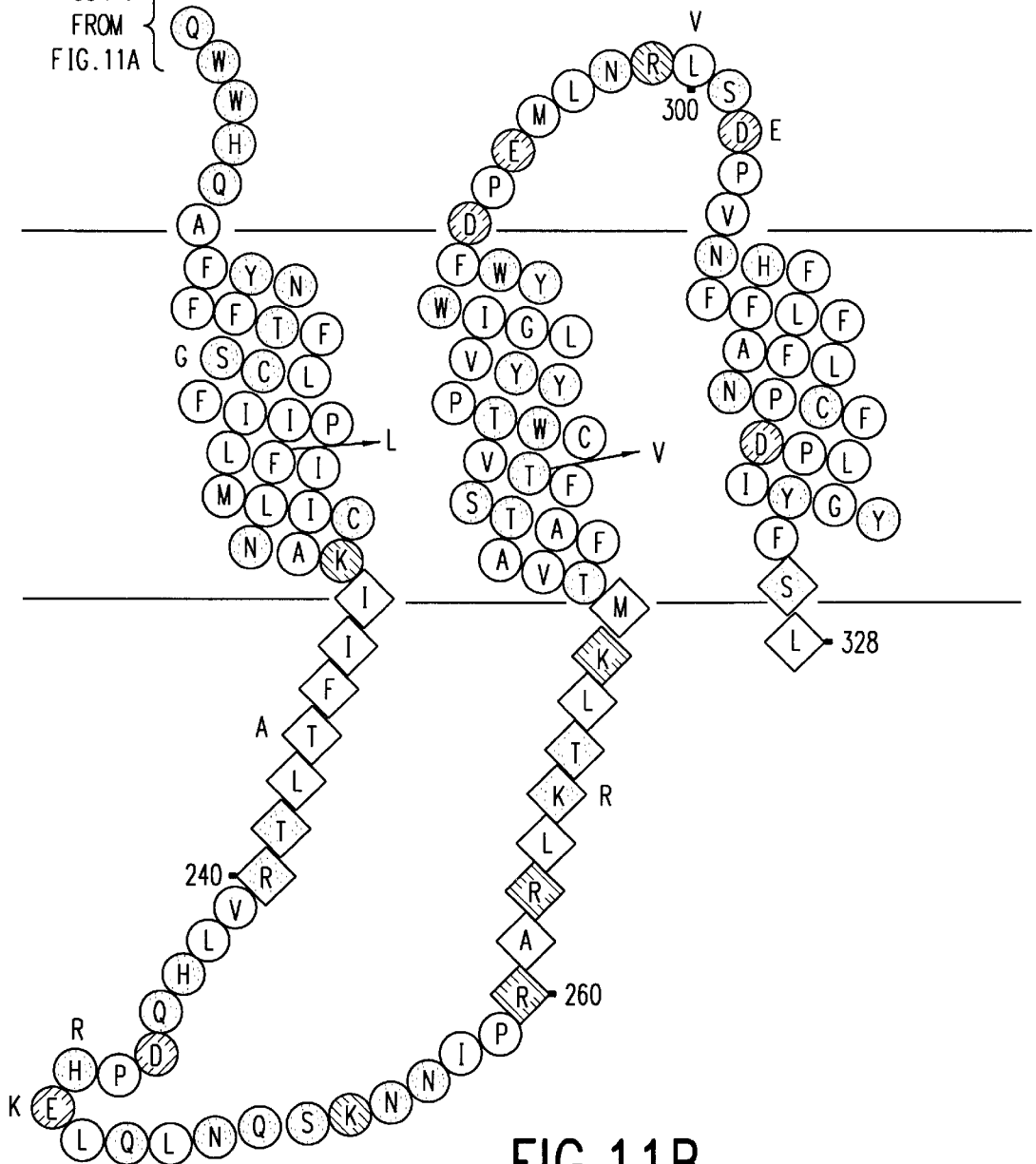

FIGS. 11A–11B. Schematic of human GnRH-R SEQ ID NO: 4.

5. DETAILED DESCRIPTION OF THE INVENTION

The present invention relates to the cloning and expression of murine and human GnRH-R. The GnRH-R, which plays a pivotal role in the reproductive system, is characterized by seven transmembrane domains characteristic of G protein-coupled receptors, but lacks a typical intracellular C-terminus. The unusual structure and regulatory domain of the GnRH-R is responsible for the unique aspects of signal transduction and regulation mediated by the receptor. The GnRH-R produced herein may be used to evaluate and screen drugs and analogs of GnRH involved in receptor activation, regulation and uncoupling. Alternatively, GnRH-R DNA, oligonucleotides and/or antisense sequences, or the GnRH-R, peptide fragments thereof, is or antibodies thereto may be used in the diagnosis and/or treatment of reproductive disorders.

For clarity of discussion, the invention is described in the subsections below by way of example for the murine and human GnRH-R. However, the principles may be analogously applied to clone and express the GnRH-R of other species, and to clone and express other receptors belonging to the unique GnRH-R family, i.e., G-protein type of receptors which lack an intracellular C-terminus and bind to GnRH or analogs thereof.

5.1. The GnRH-R Coding Sequence

The nucleotide coding sequence (SEQ. ID NO: 1) and deduced amino acid sequence (SEQ. ID NO: 2) for the murine GnRH-R are depicted in FIGS. 3A–3B. The nucleotide coding sequence and deduced amino acid sequence for the human GnRH-R are depicted in FIGS. 9A–9B.

The invention covers a gene containing (a) at least one of the DNA sequences disclosed herein (as shown in FIGS. 3 and 9); (b) any DNA sequence that encodes the amino acid sequence encoded by: the DNA sequences disclosed herein (as shown in FIGS. 2 and 9); (c) any DNA sequence that hybridizes to the complement of: the coding sequences disclosed herein (as shown in FIGS. 2 and 9), under highly stringent conditions, e.g., hybridization to filter-bound DNA in 0.5 M NaHPO$_4$, 7% sodium dodecyl sulfate (SDS), 1 mM EDTA at 65°, and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), and encodes a gene product functionally equivalent to a gene product encoded by a gene of (a), above; and/or (d) any DNA sequence that hybridizes to the complement of: the coding sequences disclosed herein, (as shown in FIGS. 2 and 9), under less stringent conditions, such as moderately stringent conditions, e.g., washing in 0.2×SSC/0.1% SDS at 42° C. (Ausubel et al., 1989, supra), yet which still encodes a gene product functionally equivalent to a gene product encoded by a gene of (a), above.

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target, fingerprint, and/or pathway gene nucleic acid sequences. Further, such sequences may be used as part of ribozyme and/or triple helix sequences, also useful for target gene regulation. Still further, such molecules may be used as components of diagnostic methods whereby the presence of, or predisposition to, a GnRH-R related disorder may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein.

The longest open reading frame encodes a 327 amino acid protein of about 37,000 MW. Three consensus N-linked glycosylation sites are present, two in the N-terminus and one in the first extracellular loop (FIG. 3). Hydrophobicity analysis of the deduced protein reveals seven stretches of highly hydrophobic amino acids with 20–30% sequence similarity to other G-protein receptors, with the highest degree of homology to the interleukin-8 receptor (FIG. 4).

The GnRH-R is nearly the smallest member of the G-protein receptor superfamily, the first cytoplasmic loop of the GnRH-R is longer than any other G-protein receptor, and unlike any other G-protein receptor, it lacks a polar cytoplasmic C-terminus. While highly conserved residues are present in the GnRH-R, such as the cysteines in each of the first two extracellular loops which stabilize many receptors, several features of the GnRH-R are unusual. For example, the highly conserved transmembrane II aspartate/glutamate, which has been found to be essential for the function of many G-protein receptors, is replaced by asparagine. Another deviation from other G-protein receptors is the substitution of a serine for the conserved tyrosine located adjacent to transmembrane III. This creates a potential phosphorylation site, unique to the GnRH-R, in a domain critical for signal transduction of other G-protein receptors. Other is potential regulatory phosphorylation sites are also present (see FIGS. 3A–3B).

The invention also relates to GnRH-R genes isolated from other species, including humans. The human GnRH receptor was cloned by probing a λgt10 human pituitary cDNA library with the mouse GnRH receptor insert which had been $^{32}$P-labeled via random hexamer priming. To confirm that the isolated clone encoded a functional human GnRH-R, synthetic RNA transcripts were injected into oocytes. All RNA-injected oocytes developed large depolarizing currents upon exposure to GnRH indicating that the cloned DNA fragment encoded a functional receptor.

The nucleotide coding sequence (SEQ. ID. NO: 3) and deduced amino acid sequence (SEQ. ID. NO: 4) for the human GnRH-R are depicted in FIGS. 9A–9B. sequencing of the human clone identified a 2160 bp insert containing a 984 bp open reading frame. The open reading frame encodes a 328 amino acid protein with 90% identity to the predicted sequence of the mouse receptor.

Hydrophobicity analysis identified the seven hydrophobic domains characteristics of G-protein coupled receptors. As was found for the predicted structure of the mouse receptor, the human GnRH-R lacks essentially any C-terminal intracellular domain.

Two potential N-linked glycosylation sites are present, one in each of the first extracellular domains. Several cytoplasmic serine and threonine residues are found on intracellular domains and may serve as regulatory phosphorylation sites (FIGS. 11A–11B SEQ ID NO: 4).

Northern blot analysis, utilizing radioactively labelled human GnRH-R as a probe, identified a transcript of roughly 4.7 kb in human pituitary poly(A) RNA (FIG. 10). No signal was detected in poly(A) RNA purified from human testis or with a human β-actin cDNA control.

To determine the extent of the 5' and 3' -untranslated domains of the RNA, PCR analysis of the phage isolates from the primary library screening was undertaken. An antisense oligonucleotide primer representing sequence near the 5'-end of the GnRH-R cDNA insert or a sense primer near the 3'-end of the same sequence was used in conjunction with primers designed against the adjacent GTI-cloning site to map the unpurified clones. The longest PCR products identified had ~1.3 kb of additional 5'-sequence and 0.3 kb of additional 3'-sequence. These data suggest that the GnRH-R mRNA contains at least 1.3 kb of 5'-untranslated sequence and 1.5 kb of 3'-untranslated sequence. Based on the Northern blot data, this suggests that additional untranslated sequence (<1 kb) is not contained in any of the clones isolated.

The invention also relates to GnRH-R genes isolated from other species in which GnRH-R activity exists. Members of the GnRH-R family are defined herein as those receptors that bind GnRH. Such receptors may demonstrate about 80% homology at the nucleotide level, and even 90% homology at the amino acid level in substantial stretches of sequences located in regions outside the transmembrane domains.

Cloning of other receptors in the GnRH-R family may be carried out in a number of different ways. For example, the murine and human sequence can be used to design degenerate or fully degenerate oligonucleotide probes which can be used as PCR probes or to screen cDNA libraries derived from appropriate cells which express the GnRH-R, or genomic libraries. The N-terminus and cytoplasmic loops (both intracellular and extracellular) of the murine and human sequences depicted in FIGS. 3A–3B and FIGS. 11A–11B; SEQ ID NO: 4, respectively, may advantageously be used to design such oligonucleotide probes, as these regions should be relatively conserved within the GnRH-R family.

Alternatively, a bacteriophage cDNA library may be screened, under conditions of reduced stringency, using a radioactively labeled fragment of the human or murine GnRH-R clone to isolate GnRH-R related proteins. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

In accordance with the invention, nucleotide sequences which encode a GnRH-R, fragments, fusion proteins or functional equivalents thereof, may be used to generate recombinant DNA molecules that direct the expression of the GnRH-R, or a functionally active peptide, fusion protein or functional equivalent thereof, in appropriate host cells. Alternatively, nucleotide sequences which hybridize to portions of the GnRH-R sequence may also be used in nucleic acid hybridization assays, Southern and Northern blot analyses, etc.

Due to the degeneracy of the genetic code, other DNA sequences which encode substantially the GnRH-R amino acid sequence, e.g., such as the murine sequence (SEQ. ID NO: 2) depicted in FIGS. 3A–3B, or the human sequence depicted in FIGS. 9A–9B (SEQ. ID NO: 4), or a functional equivalent, may be used in the practice of the present invention for the cloning and expression of the GnRH-R. Such DNA sequences include those which are capable of hybridizing to the murine or human GnRH-R sequence under stringent conditions, or which would be capable of hybridizing under stringent conditions but for the degeneracy of the genetic code. The stringency conditions may be adjusted in a number of ways. For example, when performing polymerase chain reactions (PCR), the temperature at which is annealing of primers to template takes place or the concentration of $MgCl_2$ in the reaction buffer may be adjusted. When using radioactively labeled DNA fragments or oligonucleotides to probe filters, the stringency may be adjusted by changes in the ionic strength of the wash solutions or by carefully controlling the temperature at which the filter washes are carried out.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the GnRH-R sequence, which result in a silent change thus producing a functionally equivalent GnRH-R. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. As used herein, a functionally equivalent GnRH-R refers to a receptor which binds to GnRH, but not necessarily with the same binding affinity of its counterpart native GnRH-R.

The DNA sequences of the invention may be engineered in order to alter the GnRH-R coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the GnRH-R coding sequence to eliminate the N-linked glycosylation site; e.g. in the murine sequence this may be accomplished by altering one or more glycosylation sites indicated in FIGS. 3A–3B. In another embodiment for the invention, the GnRH-R or a modified GnRH-R sequence may be ligated to a heterologous sequence to encode a fusion protein. The fusion protein may be engineered to contain a cleavage site located between the GnRH-R sequence and the heterologous protein sequence, so that the GnRH-R can be cleaved away from the heterologous moiety.

In an alternate embodiment of the invention, the coding sequence of GnRH-R could be synthesized in whole or in part, using chemical methods well known in the art. See, for example, Caruthers, et al., 1980, Nuc. Acids Res. Symp. Ser. 7:215–233; Crea and Horn, 180, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the GnRH-R amino acid sequence in whole or in part. For example, peptides can be synthesized by solid phase techniques, cleaved from the resin, and purified by preparative high performance liquid chromatography (e.g., see Creighton, 1983, Proteins Structures And Molecular Principles, W. H. Freeman and Co., N.Y. pp. 50–60).

The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49).

5.2. Expression of the GnRH-R

In order to express a biologically active GnRH-R, the nucleotide sequence coding for GnRH-R, or a functional equivalent as described in Section 5.1 supra, is inserted into an appropriate expression vector, i.e., a vector which contains the necessary elements for the transcription and translation of the inserted coding sequence. The GnRH-R gene products as well as host cells or cell lines transfected or transformed with recombinant GnRH-R expression vectors can be used for a variety of purposes. These include but are not limited to generating antibodies (i.e., monoclonal or polyclonal) that bind to the receptor, including those that competitively inhibit GnRH binding and "neutralize" GnRH activity; the screening and selection of GnRH analogs or drugs that act via the GnRH-R; etc.

5.2.1. Expression Systems

Methods which are well known to those skilled in the art can be used to construct expression vectors containing the GnRH-R coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the GnRH-R coding sequence. These include but are not limited to microorganisms such as bacteria transformed with recombinant bacteriophage DNA, plasmid DNA or cosmid DNA expression vectors containing the GnRH-R coding sequence; yeast transformed with recombinant yeast expression vectors containing the GnRH-R coding sequence; insect cell systems infected with recombinant virus expression vectors (e.g., baculovirus) containing the GnRH-R coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the GnRH-R coding sequence; or animal cell systems infected with recombinant virus expression vectors (e.g., adenovirus, vaccinia virus) including cell lines engineered to contain multiple copies of the GnRH-R DNA either stably amplified (e.g., CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the GnRH-R DNA SV40-, BPV- and EBV-based vectors may be used with an appropriate selectable marker.

In bacterial systems a number of expression vectors may be advantageously selected depending upon the use intended for the GnRH-R expressed. For example, when large quantities of GnRH-R are to be produced for the generation of antibodies, vectors which direct the expression of high levels of fusion protein products that are readily purified may be desirable. Such vectors include but are not limited to the E. coli expression vector pUR278 (Ruther et al., 1983, EMBO J. 2:1791), in which the GnRH-R coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the GnRH-R coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc.

For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express GnRH-R is an insect system. In one such system, *Autographa californica* nuclear polyhidrosis virus (AcNPV) is used as a vector to express foreign genes. The virus grows in *Spodoptera frugiperda* cells. The GnRH-R coding sequence may be cloned into non-essential regions (for example the polyhedrin gene) of the virus and placed under control of an AcNPV promoter (for example the polyhedrin promoter). Successful insertion of the GnRH-R coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the GnRH-R coding sequence may be ligated to an adenovirus transcription/translation control complex, e.g., the late promoter and tripartite leader sequence. This chimeric gene may then be inserted in the adenovirus genome by in vitro or in vivo recombination.

Insertion in a non-essential region of the viral genome (e.g. region E1 or E3) will result in a recombinant virus that is viable and capable of expressing GnRH-R in infected hosts. (E.g., See Logan & Shenk, 1984, Proc. Natl. Acad. Sci. (USA) 81:3655–3659). Alternatively, the vaccinia 7.5K promoter may be used. (E.g., see Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted GnRH-R coding sequences. These signals include the ATG initiation codon and adjacent sequences. In cases where the entire GnRH-R gene, including its own initiation codon and adjacent sequences, is inserted into the is appropriate expression vector, no additional translational control signals may be needed. However, in cases where only a portion of the GnRH-R coding sequence is inserted, exogenous translational control signals, including the ATG initiation codon, must be provided. Furthermore, the initiation codon must be in phase with the reading frame of the GnRH-R coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the GnRH-R may be engineered. Rather than using expression vectors which contain viral origins of replication, host cells can be transformed with the GnRH-R DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the GnRH-R on the cell surface, and which respond to GnRH mediated signal transduction. Such engineered cell lines are particularly useful in screening GnRH analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

In a specific embodiment, described herein, the human GnRH-R cDNA was subcloned into an expression vector, pSV2A, containing the SV40 early promoter. COS-1 cells were transiently transfected with the pSV2A-human GnRH-R construct using the DEAE-dextran method of transfection (Keown, W. A. et al., 1990, in Methods of Enzymology, Vl. 185 (Goeddel, D. V., ed.) pg. 527–537 Academic Press, New York). Experiments, using membranes from COS-1 transfected cells, indicated that the heterologously expressed receptor was capable of binding GnRH. Ligand binding was also found to be coupled to inositol phosphate metabolism indicating further that the transfected COS-1 cells expressed a functional human GnRH-R.

5.2.2. Identification of Transfectants or Transformants that Express the GnRH-R The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of GnRH-R mRNA transcripts in the host cell; and (d) detection of the gene product as measured by immunoassay or by its biological activity.

In the first approach, the presence of the GnRH-R coding sequence inserted in the expression vector can be detected by DNA-DNA or DNA-RNA hybridization using probes comprising nucleotide sequences that are homologous to the GnRH-R coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the GnRH-R coding sequence is inserted within a marker gene sequence of the vector, recombinants containing the GnRH-R coding sequence can be identified by the absence of the marker gene function. Alternatively, a marker gene can be placed in tandem with the GnRH-R sequence under the control of the same or different promoter used to control the expression of the GnRH-R coding sequence. Expression of the marker in response to induction or selection indicates expression of the GnRH-R coding sequence.

In the third approach, transcriptional activity for the GnRH-R coding region can be assessed by hybridization assays. For example, RNA can be isolated and analyzed by Northern blot using a probe homologous to the GnRH-R coding sequence or particular portions thereof. Alternatively, total nucleic acids of the host cell may be extracted and assayed for hybridization to such probes.

In the fourth approach, the expression of the GnRH-R protein product can be assessed immunologically, for example by Western blots, immunoassays such as radioimmuno-precipitation, enzyme-linked immunoassays and the like. The ultimate test of the success of the expression system, however, involves the detection of the biologically active GnRH-R gene product. A number of assays can be used to detect receptor activity including but not limited to GnRH, or GnRH analog, binding assays; and GnRH biological assays using engineered cell lines as the test substrate.

In a specific embodiment described herein, cell membranes were prepared from COS-1 cells transfected with a recombinant expression vector containing the human GnRH-R cDNA. Expression of the human GnRH-R was detected using a $^{125}$I labeled GnRH analog. In addition the expression of biologically active GnRH-R could be detected in transfected cells by measuring levels of GnRH-stimulated inositol phosphate (IP) production as described in Section 7.1.5.

5.2.3. Recovery of the GnRH-R

Once a clone that produces high levels of biologically active GnRH-R is identified, the clone may be expanded and used to produce large amounts of the receptor which may be purified using techniques well-known in the art including, but not limited to immunoaffinity purification, chromatographic methods including high performance liquid chromatography, affinity chromatography using immobilized ligand such as GnRH or analogs thereof bound to beads, immunoaffinity purification using antibodies and the like.

Where the GnRH-R coding sequence is engineered to encode a cleavable fusion protein, purification may be readily accomplished using affinity purification techniques.

For example, a collagenase cleavage recognition consensus sequence may be engineered between the carboxy terminus of GnRH-R and protein A. The resulting fusion protein may be readily purified using an IgG column that binds the protein A moiety. Unfused GnRH-R may be readily released from the column by treatment with collagenase. Another example would be the use of pGEX vectors that express foreign polypeptides as fusion proteins with glutathionine S-transferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In this aspect of the invention, any cleavage site or enzyme cleavage substrate may be engineered between the GnRH-R sequence and a second peptide or protein that has a binding partner which could be used for purification, e.g., any antigen for which an immunoaffinity column can be prepared.

5.3. Generation of Antibodies that Define the GnRH-R

Various procedures known in the art may be used for the production of antibodies to epitopes of the recombinantly produced GnRH-R. Neutralizing antibodies, i.e., those which compete for the GnRH binding site of the receptor are especially preferred for diagnostics and therapeutics. Antibodies which define viral serological markers would be preferred for diagnostic uses. Such antibodies include but are not limited to polyclonal, monoclonal, chimeric, single chain, Fab fragments and fragments produced by an Fab expression library.

For the production of antibodies, various host animals may be immunized by injection with the GnRH-R including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *corynebacterium parvum*.

Monoclonal antibodies to GnRH-R may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96).

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce GnRH-R-specific single chain antibodies.

Antibody fragments which contain specific binding sites of GnRH-R may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to GnRH-R.

5.4. Uses of the GnRH-R, DNA and Engineered Cell Lines

The GnRH-R DNA, antisense oligonucleotides, GnRH-R expression products, antibodies and engineered cell lines described above have a number of uses for the diagnosis and treatment of reproductive disorders and in drug design and discovery.

For example, the GnRH-R DNA sequence may be used in hybridization assays of biopsies to diagnose abnormalities of GnRH-R expression; e.g., Southern or Northern analysis, including in situ hybridization assays. In therapeutic applications, antisense or ribozyme molecules designed on the basis of the GnRH-R DNA sequence may be utilized to block transportation and expression of the GnRH-R gene product. In this regard, oligonucleotides derived from the translation initiation site, e.g., between −10 and +10 regions of the GnRH-R nucleotide sequence, are preferred. Alternatively, the GnRH-R DNA could be used in gene therapy approach to introduce the normal recombinant gene into the defective cells of an individual or to correct an endogenous mutation in order to reconstitute the GnRH-R and its function.

In another embodiment of the invention, antibodies specific for the GnRH-R may be used to determine the pattern of receptor expression in biopsy tissue, or for diagnostic imaging in vivo; in such applications, "neutralizing" antibodies may be preferred. For example, an antibody conjugated to an imaging compound could be administered to a patient to "map" the locations and distribution of the GnRH-R in vivo.

In another embodiment of the invention, the GnRH-R itself, or a fragment containing its GnRH binding site, could be administered in vivo. The free GnRH-R or the peptide fragment could competitively bind to GnRH and inhibit its interaction with the native receptor in vivo.

In another embodiment of the invention, stimulation of an antibody response, specific for GnRH-R, may be used as a means of contraception. For example, various host animals may be immunized by injection with GnRH-R or GnRH-R fusion protein, leading to stimulation of their immune system and production of circulating anti-GnRH-R antibodies.

The GnRH-R and/or cell lines that express the GnRH-R may be used to screen for antibodies, peptides, organic molecules or other ligands that act as agonists or antagonists of GnRH-R activity. For example, anti-GnRH-R antibodies capable of neutralizing the activity of GnRH, may be used to inhibit GnRH-R function. Additionally, anti-GnRH-R antibodies which mimic GnRH activity may be selected for uses in reproductive disorders in which GnRH activity is diminished. Alternatively, screening of peptide libraries or organic compounds with recombinantly expressed soluble protein or cell lines expressing protein may be useful for identification of therapeutic molecules that function by inhibiting the biological activity of GnRH.

In an embodiment of the invention, engineered cell lines which express the entire coding region or its ligand binding domain may be utilized to screen and identify GnRH antagonists as well as agonists. Synthetic compounds, natural products, and other sources of potentially biologically active materials can be screened in a number of ways. The ability of a test compound to inhibit binding of GnRH or an analog thereof, to GnRH-R may be measured using standard receptor binding techniques, such as those described in Section 7.1.4. infra.

The ability of agents to prevent or mimic, the effect of GnRH binding on signal transduction responses in expressing cells may be measured. For example, responses such as modulation of second messenger production or changes in cellular metabolism, i.e., release of intracellular stores of calcium or activation of protein kinase C may be monitored. In a specific embodiment described herein, GnRH-stimulated inositol phosphate (IP) production was utilized as an indicator of GnRH-R mediated signal transduction. Assays for measuring GnRH mediated signal transduction may be performed using any of the conventional techniques developed for these purposes.

The ability of a test compound to modulate signal transduction through the GnRH-GnRH-R system may also be measured in vivo, in animal model systems. For example, transgenic animals which contain the GnRH-R DNA as the transgene may be engineered to test the effects of such agonists or antagonists in vivo. The ability of agents to prevent the effect of GnRH binding on signal transduction responses of expressing cells may be measured. For example, responses such as production of hormones, inhibition or activation of reproductive functions, or reduction in the size of hormone responsive tumors may be monitored.

5.4.1. Screening of Peptide Library with GnRH-R Protein or Engineered Cell Lines Random peptide libraries consisting of all possible combinations of amino acids attached to a solid phase support may be used to identify peptides that are able to bind to the ligand binding site of the GnRH-R. The screening of peptide libraries may have therapeutic value in the discovery of pharmaceutical agents that act to inhibit or activate the biological activity of the GnRH-R through their interaction with the receptor.

Identification of molecules that are able to bind to the GnRH-R may be accomplished by screening a peptide library with recombinant soluble GnRH-R protein. Methods for expression and purification of GnRH-R are described in Section 5.2.1., supra, and may be used to express recombinant full length GnRH-R or fragments of GnRH-R depending on the functional domains of interest. For example, the intra- and extra-cellular ligand binding domains of GnRH-R may be separately expressed and used to screen peptide libraries.

To identify and isolate the peptide/solid phase support that interacts and forms a complex with GnRH-R, the GnRH-R molecule may be labeled or "tagged." The GnRH-R protein can be labeled by conjugation to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to GnRH-R, may be performed using techniques that are routinely known in the art.

Alternatively, GnRH-R expression vectors may be engineered to express a chimeric GnRH-R protein containing an epitope for which a commercially available antibody exist. The epitope specific antibody may be tagged using methods well known in the art including labeling with enzymes, fluorescent dyes or colored or magnetic beads.

To identify peptides that are able to bind GnRH-R, the "tagged" GnRH-R conjugate is incubated with the random peptide library for 30 minutes to one hour at 22° C. to allow complex formation between GnRH-R and peptide species within the library. The library is then washed to remove any unbound GnRH-R protein.

If GnRH-R has been conjugated to alkaline phosphatase or horseradish peroxidase the whole library is poured into a petri dish containing a substrates for either alkaline phosphatase or peroxidase, for example, 5–bromo-4-chloro-3-indoyl phosphate (BCIP) or 3,3',4,4"-diaminobenzidine (DAB), respectively. After incubating for several minutes, the peptide/solid phase-GnRH-R complex changes color, and can be easily identified and isolated physically under a dissecting microscope with a micromanipulator. If a fluorescent tagged GnRH-R molecule has been used, complexes may be isolated by fluorescent activated sorting. If a chimeric GnRH-R protein expressing a heterologous epitope has been used, detection of the peptide/GnRH-R complex may be accomplished by using a labeled epitope specific antibody. Once isolated, the identity of the peptide attached to the solid phase support may be determined by peptide sequencing.

In addition to using soluble GnRH-R molecules, in another embodiment, it is possible to detect peptides that bind to GnRH-R using intact cells expressing GnRH-R. The use of intact cells is preferred for use with receptors that are multi-subunits, or labile, or with receptors that require the lipid domain of the cell membrane to be functional. Methods for generating cell lines expressing GnRH-R are described in Sections 5.2.1. and 5.2.2. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays the GnRH-R molecule can be reconstituted into liposomes which may be labeled or "tagged" and used in screening of peptide libraries as described above.

5.4.2. Screening of Compounds with GnRH-R Protein or Engineered Cell Lines

Cell lines that express GnRH-R may be used to screen for molecules that modulate GnRH-R activity or GnRH-R mediated signal transduction. Such molecules may include small organic or inorganic compounds, or other molecules that modulate GnRH-R activity or that promote or prevent the formation of GnRH-R/GnRH complex. Synthetic compounds, natural products, and other sources of potentially biologically active materials can be screened in a number of ways.

The ability of a test molecule to interfere with GnRH-GnRH-R binding and/or GnRH-R signal transduction may be measured using standard biochemical techniques. Responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes.

Cellular processes under the control of the GnRH-R/GnRH signalling pathway may include, but are not limited to, normal cellular functions such as production of hormones, and proliferation and/or differentiation of cells, in addition to abnormal or potentially deleterious processes such as unregulated cell proliferation, blocking of differentiation or cell death. The qualitative or quantitative observation and measurement of any of the described cellular processes is by techniques known in the art may be advantageously used as a means of scoring for signal transduction in the course of screening.

Various embodiments are described below for screening, identification and evaluation of compounds that interact with the GnRH-R, which compounds may affect various cellular processes under the control of the GnRH receptor signalling pathway.

The present invention includes a method for identifying a compound which is capable of modulating GnRH-R activity comprising:
  (a) contacting the compound with GnRH-R, or a functional derivative thereof, in pure or semi-pure form, in a membrane preparation, or in a whole live or fixed cell;
  (b) incubating the mixture of step (a) in the presence of GnRH, or a GnRH analog, for an interval sufficient for the compound to stimulate or inhibit the signal transduction;
  (c) measuring the signal transduction;
  (d) comparing the signal transduction activity to that of GnRH-R, incubated without the compound, thereby determining whether the compound stimulates or inhibits signal transduction.

GnRH-R, or functional derivatives thereof, useful in identifying compounds capable of modulating signal transduction may have, for example, amino acid deletions and/or insertions and/or substitutions as long as they retain significant signal transducing capacity. A functional derivative of GnRH-R may be prepared from a naturally occurring or recombinantly expressed GnRH-R by proteolytic cleavage followed by conventional purification procedures known to those skilled in the art. Alternatively, the functional derivative may be produced by recombinant DNA technology by expressing parts of GnRH-R which include functional domains in suitable cells. Functional derivatives may also be chemically synthesized. Cells expressing GnRH-R may be used as a source of GnRH-R, crude or purified, or in a membrane preparation, for testing in these assays. Alternatively, whole live or fixed cells may be used directly in those assays.

GnRH-R signal transduction activity may be measured by standard biochemical techniques or by monitoring the cellular processes controlled by the signal. For example, to assess modulation of GnRH-R activity, activation of phospholipase C or generation of inositol-1,4,5-triphosphate or diacylglycerol may be assayed after the test molecule is added to a reaction mixture containing GnRH-R. Alternatively, activation of protein kinase C or release of calcium ions from intracellular stores may be assayed.

The invention further provides for a method of screening compounds that, upon interacting with GnRH-R, elicit or trigger a signal mimicking the action of GnRH binding to the GnRH-R. Signal transduction is mimicked if the cellular processes under the control of the signalling pathway are affected in a way similar to that caused by ligand binding. Such compounds may be naturally occurring or synthetically produced molecules that activate the GnRH-R.

The invention also includes a method whereby a molecule capable of binding to GnRH-R in a chemical or biological preparation may be identified comprising:
  (a) immobilizing GnRH-R, or functional fragments thereof, to a solid phase matrix;
  (b) contacting the chemical or biological preparation with the solid phase matrix produced in step (a), for an interval sufficient to allow the compound to bind;
  (c) washing away any unbound material from the solid phase matrix;
  (d) detecting the presence of the compound bound to the solid phase, thereby identifying the compound.

The above method may further include the step of:
  (e) eluting the bound compound from the solid phase matrix, thereby isolating the compound.

The term "compound capable of binding to GnRH-R" refers to any naturally occurring or synthetically produced molecule which interacts with GnRH-R. Such a compound may directly or indirectly modulate GnRH-R signal transduction and may include molecules that are natively associated with the intracellular domain of GnRH-R inside a cell. Examples of such compounds are (i) a natural substrate of GnRH-R; (ii) a naturally occurring molecule which is part of the signalling complex; and/or a naturally occurring signalling molecule produced by other cell types.

5.5. Uses of GnRH-R Analogs in Treatment of Proliferative Disorders

In an embodiment of the invention, drugs involved in GnRH-R modulation, by either agonists or antagonists activity, may be useful for treatment of proliferative disorders such as cancers. For example, drugs which modulate the activity of the GnRH-R may be utilized to regulate the proliferation of GnRH responsive cancer cells that express the GnRH-R on their cell surface.

Regulation of hormone levels, through mediation of GnRH-R activity, may also be useful for treatment of hormone responsive tumors. In another embodiment of the invention drugs that exhibit either agonist or antagonist GnRH-R activity may be used to indirectly modulate the abnormal proliferation of hormone responsive tumors. The production of hormones such as estrogen and testosterone may be regulated through modulation of GnRH-R activity. For example, modulators of GnRH-R activity may be administered to male prostate cancer patients for the desired effect of reducing serum testosterone levels. In addition, modulators of GnRH-R may be administered to female breast cancer patients to reduce levels of estrogen activity.

5.6. Pharmacological Preparations

The particular peptides, proteins, organic compounds or antibodies that modulate GnRH-R receptor signal transduction can be administered to a patient either by itself, or in pharmaceutical compositions where it is mixed with suitable carriers or excipient(s).

Depending on the specific conditions being treated, these agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, or, in the case of solid tumors, directly injected into a solid tumor.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes.

Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The is push-fit capsules can contain the active ingredients in a mixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Compositions comprising a compound of the invention formulated in a compatible pharmaceutical carrier may be prepared, placed in an appropriate container, and labelled for treatment of an indicated condition. Suitable conditions indicated on the label may include treatment of reproductive disorders and proliferative disorders such as cancers. In addition, the compounds of the invention may be used as a method of contraception.

A preferred pharmaceutical carrier for hydrophobic compounds of the invention is a cosolvent system comprising benzyl alcohol, a nonpolar surfactant, a water-miscible organic polymer, and an aqueous phase. A preferred cosolvent system is the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene is glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. certain organic solvents such as DMSO also may be employed, although usually at the cost of greater toxicity.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the GnRH-R modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of GnRH-R activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the GnRH-R receptor-inhibitory effects. Usual patient dosages for systemic administration range from 1–2000 mg/day, commonly from 1–250 mg/day, and typically from 10–150 mg/day. Stated in terms of patient body weight, usual dosages range from 0.02–25 mg/kg/day, commonly from 0.02–3 mg/kg/day, typically from 0.2–1.5 mg/kg/day. Stated in terms of patient body surface areas, usual dosages range from 0.5–1200 mg/m$^2$/day, commonly from 0.5–150 mg/m$^2$/day, typically from 5–100 mg/m$^2$/day.

Dosage amount and interval may be adjusted individually to provide plasma levels of the active moiety which are sufficient to maintain the GnRH-R receptor-inhibitory effects. Usual average plasma levels should be maintained within 50–5000 μg/ml, commonly 50–1000 μg/ml, and typically 100–500 μg/ml.

Alternately, one may administer the compound in a local rather than systemic manner, for example, via injection of the compound directly into a tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

6. EXAMPLE

Cloning of a Functional Murine GnRH-R

The subsections below describe the cloning of a complementary DNA representing the mouse GnRH-R and confirm its identity using Xenopus oocyte expression. Injection of sense RNA transcript leads to the expression of a functional, high-affinity GnRH-R. Expression of the GnRH-R using gonadotrope cell line RNA, however, is blocked by an antisense oligonucleotide. In situ hybridization in the rat anterior pituitary reveals a characteristic GnRH-R distribution. The nucleotide sequence encodes a 327 amino acid protein which has the seven putative transmembrane domains characteristic of G protein-coupled receptors, but which lacks a typical intracellular C-terminus. The unusual structure and novel potential regulatory domain of the GnRH-R may explain unique aspects of its signal transduction and regulation.

6.1. Materials and Methods

Drugs were obtained from the following sources: the GnRH antagonist [D-Phe$^{26}$,Pro$^3$]-GnRH (Bachem, Torrance, Calif.), buserelin (D-Ser(But)$^6$,Pro$^9$-N-ethylamide GnRH) Hoerchst-Roussel Pharmaceuticals (Somerville, N.J.). All other chemicals were from Sigma Chemical Co. (St. Louis, Mo.). All animal care was in accordance with the NIH Guide for the Care and Use of Laboratory Animals.

6.1.1. Oocyte Micro-Injection and Recording

Adult female Xenopus laevis (Nasco, Ft. Atkinson, Wis.) were kept at 18–20° C. and a day/night cycle of 15h/9h. Oocytes were prepared for injection and the responses recorded as previously described (Sealfon et al., 1990, Mol. Endocrinol 4: 119–124). Cells were placed in a 0.5 ml bath and voltage clamped at −70 mV using standard two electrode technique (Dascal, 1987, CRC Crit. Rev. Biochem. 417: 47–61). Peptide ligands were diluted in the perfusion buffer and introduced into the bath. The clamp current was recorded using a chart recorder. Reversal potentials were determined by continuous ramping from −70 to +10 mV over 2 seconds with and without agonist through an IBM PC/AT system using the TL-1 interface and pCLAMP software from Axon Instruments (Burlingame, Calif.).

6.1.2. PCR Cloning and Hybrid Arrest Screening

RNA preparation and cDNA synthesis were performed as previously described (Sealfon et al., 1990, Mol. Endocrinol 4: 119–124; Snyder et al., 1991, Neurosci Lett 122: 37–40). Subclones for hybrid arrest screening were isolated using PCR with a variety of degenerate oligonucleotides corresponding to conserved transmembrane domains of the GPR superfamily. The oligonucleotides used to isolate the group of subclones including WZ7, modified from sequences of published oligomers (Zhou et al., 1990, Nature 347: 76–80), corresponded to transmembrane III (5'-GAGTCGACCTGTG(CT)G(CT)(GC)AT(CT)(AG)CNNT (GT)GAC(AC)G(C G)TAC-3') and transmembrane VI (5'-CAGAATTCAG(AT)AGGGCANCCAGCAGAN(CG) (AG)(CT)GAA-3'). PCR was performed at low stringency. A portion of the reaction was reamplified at high stringency, digested with restriction enzymes, subcloned into pBluescript II KS+ (Stratagene) and sequenced. For hybrid-arrest assay, an antisense oligonucleotide corresponding to transmembrane II of the 5HT$_{1C}$ receptor (5'-ATCAGCAATGGCTAG-3') (Julius et al., 1988, Science 241: 558–564) and an oligonucleotide corresponding to WZ7 (5'-AGCATGATGAGGAGG-3') were synthesized. A mixture of αT3-1 (1 mg/ml) and rat brain total RNA 1 mg/ml) was preincubated with antisense oligonucleotide (100 μg/ml) for 10 minutes at 37° C. in a buffer containing 200mM NaCl and 5 mM Tris, pH 7.4 in a 3 μl volume. Xenopus oocytes were injected with 50 nl of the mixture and incubated for 48 hours before recording.

6.1.3. Library Screening and Sequencing

10$^6$ plaques of a UniZap (Stratagene) αT3-1 cDNA library were screened with the insert of WZ7 which had been $^{32}$P-labelled by random hexamer primers. 40 positive plaques were identified and 7 purified on secondary and tertiary screening. WZ25 was subcloned into pBluescript II SK+ by helper phage excision and both strands sequenced by the dideoxy-chain termination method with Sequenase T7 DNA polymerase (USB). Sequence was further confirmed by resequencing both strands using taq polymerase labelling and an Applied Biosystems automated sequencer. To exclude the possibility that the predicted cytoplasmic C-terminus was truncated due to a mutation in WZ25, the 3' sequence was confirmed in two additional independent clones. The nucleotide and amino acid sequence were analyzed using the Wisconsin GCG package on a VAX computer and MacVector (IBI) on a microprocessor.

6.1.4. Characterization of WZ25RNA Transcript

WZ25 in pBluescript II SK+ (Stratagene) was linearized and capped RNA transcript synthesized using T3 RNA polymerase (Stratagene). Oocytes were injected with 1.25 ng of the resulting transcript and incubated for 48 hours before recording. Oocytes were pretreated with either buffer or a GnRH antagonist (antagonist 6: [Ac-D-Nal(2)$^1$,D,α-Me-pCl-Phe$^2$,D-Trp$^3$,D-Arg$^6$,D-Ala$^{10}$]GnRH; antagonist 27: [Ac-D-Nal(2)$^1$,D-α-Me-pCl-Phe$^2$, D-Trp$^3$,N-ε-lpr-Lys$^5$, D-Tyr$^6$,D-Ala$^{10}$]GnRH; ref. (Cander Spuy et al., 1987, In: Vickery BH and Nestor JJ (eds) LHRH and its Analogs: Contraceptive and Therapeutic Applications. NTP Press, Lancaster, England) for 3 minutes prior to GnRH administration. To confirm receptor expression, oocytes were re-exposed to GnRH after a three minute washout of antagonist.

6.1.5. Radioligand Binding Assay

For membrane preparation, 500 oocytes were each injected with 2.5 ng synthetic WZ25 RNA. After 48 hours, oocyte membranes were prepared as described (Kobilka et al., 1987, J. Biol. Chem. 262: 15796–15802) and resuspended in binding buffer containing 10 mM HEPES, 1 mM EDTA, and 0.1% bovine serum albumin to give a final concentration of 20 oocytes/ml. The receptor binding assay using $^{125}$I-[D-Ala$^6$, NaMe-Leu$^7$, Pro$^9$-NHEt]GnRH (GnRH-A) was based on that previously described for rat and sheep pituitary membranes (Millar et al., 1989, J. Biol. Chem. 264: 21007–21013). The binding in the presence of 10$^{-6}$M GnRH analogue was considered to represent non-specific binding. Average Bo (maximal binding) and nonspecific binding values were 1429 and 662 cpm, respectively. The dissociation constant (Kd) for GnRH-A and GnRH was determined using Enzfitter (Elsevier-BIOSOFT).

6.1.6. Solution Hybridization, Northern Blot Analysis, and In Situ Hybridization A 399 nucleotide $^{32}$P-labelled GnRH-R and a 117 nucleotide 1B15 (cyclophilin internal standard) antisense cDNA probe were synthesized and hybridized to RNA in solution using described methods (Autelitano et al., 1989, Mol. Cell. Endo. 67: 101–105). Northern blot analysis using poly(A)$^+$ αT3-1 RNA was performed as described (Sambrook et al., 1989, Molecular Cloning: A Laboratory Manual. Cold Spring Harbor Laboratory Press, Cold Spring Harbor, N.Y.). In situ hybridization using $^{35}$S-UTP labeled cRNA was performed on free-floating pituitary sections following published methods (Gall & Isackson, 1989, Science 245: 758–761). Sections were mounted and exposed to Amersham Beta-max film for 3 days or dipped in radioactive emulsion and developed after 17 days.

6.2. Results

6.2.1. cDNA Cloning of a Functional Murine GnRH-R

RNA from the mouse gonadotrope cell line, αT3-1 [5], which directs the expression of a functional GnRH-R in Xenopus oocytes (Sealfon et al., 1990, Mol. Endocrinol 4: 119–124), was used to synthesize cDNA for PCR with degenerate oligonucleotides corresponding to conserved motifs of the G protein-coupled receptors (GPRs; see Probst et al., 1992, DNA and Cell Biol. 11: 1–20). PCR products were subcloned and sequenced, and antisense oligomers synthesized for a hybrid-arrest assay (Kawashi, 1985, Nuc. Acids Res. 13: 4991–5004). An oligonucleotide corresponding to clone WZ7, when co-injected with α-T3-1 and rat brain RNA, completely abolished the expression of the GnRH-R in oocytes but did not affect expression of the brain 5HT$_{1C}$ receptor (FIGS. 1A–1B). A second antisense oligonucleotide, representing a different segment of WZ7, also completely and specifically eliminated GnRH-R expression in all oocytes tested (n=16). Clone WZ7 was used as a probe to screen an αT3-1 bacteriophage cDNA library and seven positive plaques were purified.

To test whether the clone with the largest insert of 1.3 kb, WZ25, encodes a functional GnRH-R, it was subcloned for RNA synthesis and oocyte expression. All synthetic RNA-injected oocytes (n>50), when exposed to GnRH, demonstrated a large depolarizing response characteristic of GnRH-R expression (FIGS. 2A–2B). The reversal potential (V$^r$) and calcium-dependence of the response to GnRH induced in oocytes by WZ25 RNA transcript were similar to those previously obtained using αT3-1 RNA (Sealfon et al., 1990, Mol. Endocrinol 4: 119–124). The V$_r$ of the current elicited by GnRH was −27±0.79 mV (n=7), consistent with that of the chloride ion in oocytes (Barish, 1983, J. Physiol. 342: 309–325). The GnRH-elicited response was completely abolished by preloading the oocyte with 5 mM EGTA one hour before recording (n=4), but was not significantly affected by the absence of Ca$^2$+ in the perfusate (n=7). Thus the receptor expressed from clone WZ25 exhibited a response mediated through the activation of the oocyte's calcium-dependent chloride current by intracellular calcium, as is characteristic of receptors that cause phosphatidylinositol hydrolysis (see Dascal, 1987, CRC Crit. Rev. Biochem. 417: 47–61). The pharmacology of the response obtained was in agreement with expression of the mammalian GnRH-R. The GnRH agonist [D-Ser(t-Bu)$^6$,Pro$^9$-NHEt]GnRH (100 nM buserelin, n=6) elicited a depolarizing current in RNA-injected oocytes. In the presence of equimolar week GnRH antagonist [D-Phe$^{2,6}$, Pro$^3$]GnRH, there was a 60% reduction in the response to GnRH, in comparison with the response to GnRH alone (1880±551 nA, n=5, and 4756±1082 nA, n=4, respectively). Two potent GnRH antagonists completely eliminated the GnRH-elicited current (FIG. 2A).

To further characterize the receptor encoded by this cDNA clone, radioligand binding assays were performed on membranes purified from oocytes injected with the WZ25 RNA transcript. The GnRH agonist [D-Ala$^6$, NαMe-Leu$^7$, Pro$^9$-NHEt]GnRH (GnRH-A) bound with high affinity to membranes of oocytes injected with synthetic RNA (FIG. 2B). Displacement of $^{125}$I-GnRH-A by GnRH-A revealed similar Kds of 4.5 and 2.9 nM in WZ25 RNA-injected oocyte membranes and αT3-1 cell membranes respectively. Displacement by GnRH of GnRH-A bound to the cloned receptor was an order of magnitude less effective, as has been previously reported for αT3-1 membranes (Horn et al., 1991, Mol. Endocrinol. 5: 347–355). Thus the hybrid-arrest and expression data confirm that clone WZ25 represents the mouse GnRH-R.

6.2.2. Characterization of the Coding Sequence of Murine GnRH-R

The nucleotide (SEQ. ID NO: 1) and corresponding predicted amino acid sequence (SEQ. ID NO: 2) of clone WZ25 are shown in FIGS. 3A–3B. The longest open reading frame encodes a 327 amino acid protein (relative molecular mass, Mr=37,683). The larger size reported for the binding subunit of the solubilized rat GnRH-R, $M_r$ 50,000–60,000 (Hazum et al., 1986, J. Biol. Chem. 261: 13043–13048; Iwashita et al., 1988, J. Mol. Endocrinol. 1: 187–196), may be due to receptor glycosylation. Three consensus N-linked glycosylation sites are present, two in the N-terminus and one in the putative first extracellular loop. The first ATG is believed to represent the translation initiation site because it closely approximates a Kozak consensus sequence (Kozak, 1987, Nuc. Acids Res. 15: 8125–8148) and a second cDNA clone with additional 5' sequence contains two nonsense codons in this reading frame at positions −54 and −57. Thus translation initiating at any upstream start sites would terminate before reaching the correct open reading frame. There is no polyadenylation signal and the apparent poly(A) tail most likely represents oligo(dT) priming in the 3'-untranslated region during library construction. The functional GnRH-R cDNA isolated is 1.3 kb whereas the mRNA containing this sequence is approximately 4.6 kb as determined by sucrose gradient (Sealfon et al., 1990, Mol. Endocrinol 4: 119–124) and northern blot analysis (FIG. 5B). PCR analysis of 40 positive plaques identified by primary library screening suggests that the GnRH-R mRNA contains both additional and additional 3'-untranslated sequence.

Hydrophobicity analysis of the deduced protein demonstrates seven stretches of highly hydrophobic amino acids with 20–30% sequence similarity to other GPRs with the highest degree of homology to the interleukin-8 receptor (FIGS. 4A–4C). While several highly conserved residues are noted in the GnRH-R, such as the cysteines present in each of the first two extracellular loops which stabilize many receptors, several features of the GnRH-R are unusual. For example, the highly conserved transmembrane II aspartate/glutamate, which has been found to be essential for the function of many GPRs, is replaced by an asparagine. The GnRH-R is nearly the smallest member of the GPR superfamily and, unlike any other GPR, it lacks a polar cytoplasmic C-terminus. The putative first cytoplasmic loop is longer than any other GPR. Unique among GPRs, the GnRH-R may activate via dimerization (Conn et al., 1982, Nature 296: 653–655; Gregory & Taylor, 1982, Nature 300: 269–271). Its unusual structure may subserve this proposed mechanism of activation.

Another deviation from other GPRs is the substitution of serine for the conserved tyrosine located adjacent to transmembrane III. This creates a potential phosphorylation site, unique to the GnRH-R, in a domain critical for signal transduction of other GPRs. Phosphorylation of the C-terminus, which is absent in the GnRH-R, contributes to desensitization of several GPRs (see Probst et al., 1992, DNA and Cell Biology 11: 1–20). It will be interesting to determine whether the novel phosphorylation site of the GnRH-R mediates receptor desensitization. Other potential regulatory phosphorylation sites are also present (FIGS. 3A–3B).

The presence of GnRH-R mRNA in a variety of neuroendocrine cell lines was studied by solution hybridization/nuclease protection assay (FIG. 5A). GnRH-R mRNA was detected in αT3-1 cells and in mouse pituitary, but not in GnRH neuron-derived (GT-1), corticotroph (AtT20) or somatolactotroph (GH3) cell lines at the limits of detection of the assay. The absence of detectable GnRH-R mRNA in the GT-1 and AtT-20 cell lines has been confirmed using higher concentrations of RNA in the solution-hybridization/ nuclease protection assay (Dr. Andrea C. Gore, unpublished data). FIG. 5C shows the distribution of the GnRH-R mRNA in rat anterior pituitary. Labelling was heterogeneously distributed throughout the gland, a pattern previously observed by GnRH-R autoradiography (Badr & Pelletier, 1988, Neuropeptides 11: 7–11). Bright-field and dark-field microscopy reveals clustering of the cells expressing the GnRH-R mRNA (FIGS. 5 E,F).

7. EXAMPLE

Cloning and Characterization of Human GnRH-R

The subsections below describe the cloning of complementary DNA representing the human GnRH-R and confirms its identity using Xenopus oocyte expression. In addition, the human GnRH-R was expressed in COS-1 cells and was shown to be functionally active.

7.1. Materials and Methods

7.1.1. Cloning of Human GnRH-R 1.2 million plaques of a GT10 human pituitary cDNA library (Clontech) were probed at high stringency (Sambrook et al., 1989 Molecular Cloning: A Laboratory Manual, Cold Spring Harbor Laboratory Press, Cold Spring Harbor, N.Y.) with the mouse GnRH-R insert (Tsutsumi et al., 1992 Mol. Endocrinol. 6:1163–1169) which had been $^{32}$P-labeled via random hexamer priming. Thirty-two positive plaques were identified on duplicate filters; ten were selected for further characterization and six successfully purified through subsequent screening. The clone with the largest insert was subcloned into the EcoRI site of pBluescript II SK$^+$ (construct LC27-4) and both strands repeatedly sequenced on an Applied Biosystems automated sequencer (Foster City, Calif., USA) using synthetic oligonucleotide primers. The sequence was analyzed using the Wisconsin GCG package on a VAX computer.

7.1.2. Expression in Xenopus Oocytes

Construct LC27-4 was linearized and capped RNA transcript synthesized using T3 RNA polymerase. Oocyte preparation and electrophysiology were performed as previously described (Sealfon et al., 1990, Mol. Endocrinol. 4:119–124). Cells were injected with 1–10 ng of synthetic transcript and electrophysiology recorded via two-electrode voltage clamp 48 hours later. All agonists and antagonists were applied at a concentration of 0.2 μM. Antagonists were introduced into the bath 3 minutes prior to GnRH exposure.

The following GnRH analogs were used: GnRH-A: [D-Ala$^6$,N-Me-Leu$^7$,Pro$^9$-NHEt]GnRH; antagonist 5: [D-pGlu$^1$,D-Phe$^2$,D-Trp$^{3,6}$]GnRH; antagonist 6: [Ac-D-NaI (2)$^1$, D-α-Me-pCl-Phe$^2$, D-Trp$^3$,D-Arg$^6$,D-Ala$^{10}$]GNRH; antagonist 13: [Ac-D-NaI$^1$,D-α-4-ClPhe$^2$, D-Pal$^3$,D-Arg$^6$, D-Ala$^{10}$]GnRH; antagonist 27: [Ac-D-NaI(2)$^1$,D-α-Me-pCl-Phe$^2$, D-Trp$^3$, N-ε-ipr-Lys$^5$, D-Tyr$^6$,D-Ala$^{10}$]GnRH (Van der Spuy et al., 1987, in LHRH and its Analogs: Contraceptive and Therapeutic Applications (Vickery, B. H. and Nestor, J. J. eds) NTP Press, Lancaster. Buserelin [D-Ser(But)$^6$,Pro$^9$]GnRH) was a generous gift of Hoerchst-Roussel Pharmaceuticals (Somerville, N.J., USA).

7.1.3. Transfection of COS-1 Cells

The human GnRH-R cDNA was subcloned into an expression vector, pSV2A, containing an SV40 early promoter. COS-1 cells were transiently transfected with the pSV2A-human GnRH-R construct using the DEAE-dextran method (Keown et al., 1990, in Methods in Enzymology, VI. 185 (Goeddel, D.V., ed.) pp. 527–537, Academic Press, New York). In studies on GnRH binding, $3 \times 10^6$ cells/10 cm dish were transfected with 15 μg DNA. For studies on inositol phosphate production, $1.8 \times 10^5$ cells/well (12-well plates) were transfected with 1.5 μg DNA. Cells were assayed 48 hours after transfection.

7.1.4. Receptor Binding

Cell membranes were prepared from transfected cells with a single centrifugation step as described for rat pituitaries (Millar et al., 1989, J. Biol. Chem. 264:21007–21013). The receptor binding assay was performed as previously described (Tsutsumi et al., 1992, Mol. Endocrinol. 6:1163–1169) using 125I-GnRH-A. $10^{-7}$ M GnRH-A was used to estimated non-specific binding.

7.1.5. Stimulation of Inositol Phosphate Production

GnRH-stimulated inositol phosphate (IP) production was determined as described (Davidson et al., 1990, Endocrinology 126:80–87). Accumulation of [$^3$H]IP in the presence of LiCl was used as an index of inositol phosphate turnover. Briefly, transfected cells were labelled overnight with [$^3$H] inositol and stimulated with 1.0 μM GnRH in the presence of LiCl. The reaction was terminated by the addition of a perchloric acid solution and phytic acid. After neutralizing with KOH, the inositol phosphates were separated on a Dowex ion exchange column and counted.

7.1.6. Northern Blot and PCR Analysis

RNA was prepared from six human pituitaries (five male, one female, age 30–45) and human testis (age 80) by extraction with guanidinium thiocyanate followed by centrifugation in cesium chloride (Sambrook et al., 1989 in Molecular Cloning: A Laboratory Manual, Cold Spring Harbor Laboratory Press, Cold Spring Harbor, N.Y.). Pituitary (1.6 μg) and testis (0.9 μg) poly(A) RNA prepared using the Promega PolyA Tract mRNA isolation system was electrophoresed through a 1% agarose, 2.2 M formaldehyde gel, transferred to nitrocellulose membrane (HYbond-C extra, Amersham) in 20×SSC, and fixed under vacuum at 80° C. The insert from construct LC27-4 was labelled to a specific activity of $7.2 \times 10^8$ cpm/μg using Amersham Megaprime Labelling Kit. Blots were prehybridized (2 h) and hybridized (overnight) in 2×Pipes, 50% formamide, 0.5% SDS, 100 μg/ml herring sperm DNA at 42° C., followed by washing (final wash 0.2×SSC, 0.1% SDS 60° C. for 10 minutes). In order to delineate the extent of 5'- and 3'-untranslated sequence in the human RNA, the clones identified on duplicate filters in the primary library screening which were not purified were used as PCR templates with pairs of primers directed against the GT10 cloning site and the known human GnRH-R insert. The PCR reaction products obtained were compared with those obtained using clone LC27-4 as the PCR template on 1% agarose gels.

7.2 Results

7.2.1 Cloning and Characterization of Human GnRH-R

Sequencing of clone LC27-4 identified a 2160 bp insert (FIGS. 9A–9B SEQ ID NO: 3). The largest open reading frame (1008 bp) extends to the 5'-end of the clone. The translation initiation site is assigned to the first ATG in part because of the presence of a Kozak consensus sequence (Kozak, 1987 Nucleic Acids Res. 15:8125–8148). Because the clone characterized remains in reading frame in its entire 5'-extent, the existence of additional upstream initiation sites cannot be excluded. However, the presence of additional 5'-coding region is considered unlikely because of the high homology with the mouse receptor of which the translation initiation site can be assigned with greater certainly (Tsutsumi et al., 1992). The human receptor cDNA thus contains a 984 bp reading frame which encodes a 328 amino acid protein with 90% identity to the predicted sequence of the mouse receptor. The long 3'-untranslated region contains no polyadenylation signal.

Northern blot analysis was performed to determine the size of the full length human GnRHR RNA. The probe revealed a single band of ~4.7 kb in human pituitary poly(A) RNA (FIG. 10). No signal was detected in poly(A) RNA purified from human testis or with a human β-actin cDNA control. To determine the extent of the 5'- and 3'-untranslated domains of the RNA, PCR analysis of the phage isolates from the primary library screening was undertaken. An antisense oligonucleotide primer representing sequence near the 5'-end of the LC27-4 insert or a sense primer near the 3'-end of the same sequence was used in conjunction with primers designed against the adjacent GT1-cloning site to map the unpurified clones. The longest PCR products identified had ~1.3 of additional sequence and 0.3 kb of additional 3'-sequence (not shown). These data suggest that the GnRHR mRNA contains at least 1.3kb of 5'-untranslated sequence and 1.5 kb of 3'-untranslated sequence. Based on the Northern blot data, this suggests that additional untranslated sequence (<1 kb) is not contained in any of the clones isolated.

Hydrophobicity analysis (Kyte-Dolittle) identified the seven hydrophobic domains characteristic of G=-protein coupled receptors (see FIG. 9 SEQ ID NO: 3). As was found of the predicted structure of the mouse receptor, the human GnRHR lacks essentially any C-terminal intracellular domain. Two potential N-linked glycosylation sites are present, one in each of the first two extracellular domains. Several cytoplasmic serine and threonine residues are found on intracellular domains and may serve as regulatory phosphorylation sites.

7.2.2 Xenopus Oocyte Injections

Figure 6:
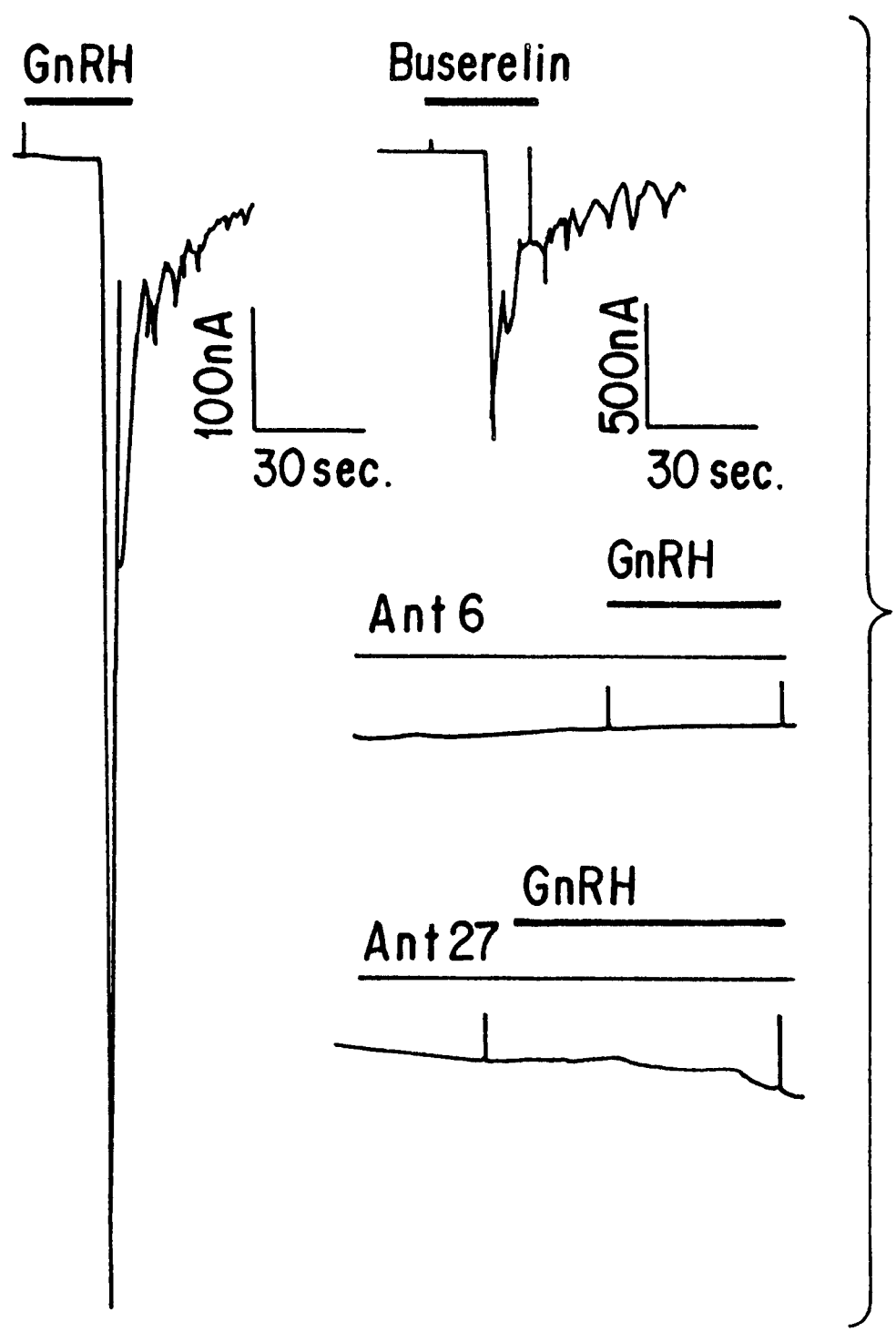
Figure 7:
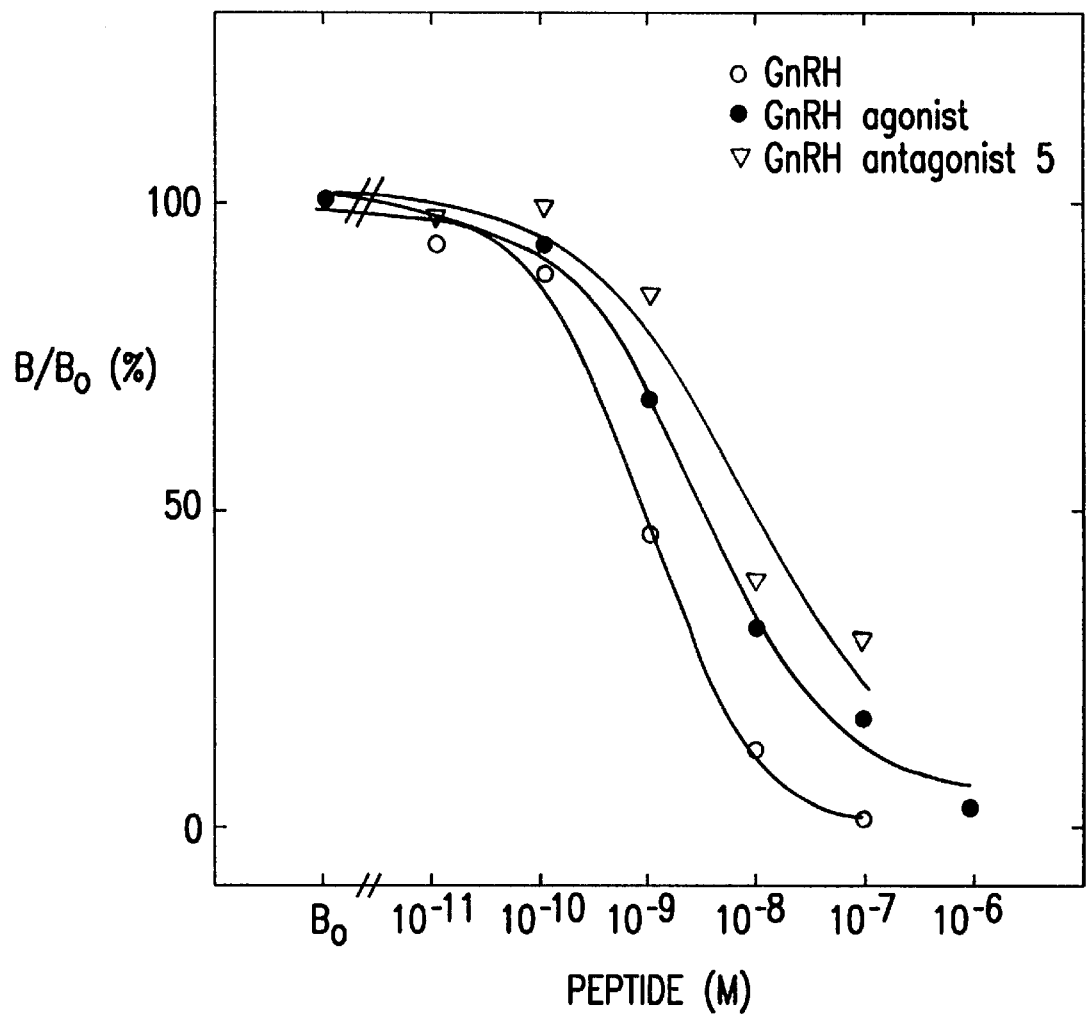

The largest clone isolated, LC27-4, contained a –2.2 kb insert. To test whether this clone encoded a functional human GnRHR, synthetic RNA transcript was injected into Xenopus oocytes. All RNA-injected oocytes developed large depolarizing currents upon exposure to $2 \times 10^{-7}$ M GnRH(n=17) or $2 \times 10^{-7}$ M buserelin (n=6; FIGS. 1A–1B) which were indistinguishable from the responses obtained following expression of the mammalian GnRHR in oocytes using tissue or cell line RNA (Sealfon et al., 1990 Mol Endocrinol. 4:119–124). These responses were completely blocked by equimolar concentrations of two potent GnRH receptor antagonists (n=5 for each; FIG. 6).

7.2.3 Expression of Human GnRH-R in COS-1 Cells

To further characterize the cloned human GnRHR, the receptor was expressed in COS-1 cells. Binding data using membranes from COS-1 cells transfected with the human GnRHR construct are presented in FIG. 7. The displacement of GnRH-A by GnRH-A, GnRH and antagonist 5 had dissociation constants of 0.97 nM, 2.8 nM and 8.4 nM respectively, values similar to those previously obtained with human pituitary membranes (Wormald et al., 1985 J. Clin. Endocrinol. Metab. 61:1190–1198).

The receptor expressed in COS-1 cells was functional and found to be coupled to inositophosphate metabolism. An ~8-fold increase in phosphoinositol metabolism was achieved at maximal receptor stimulation and the $EC_{50}$ of GnRH was ~3nM. The stimulation of PI turnover induced by $(10^{-8})$ M GnRH was inhibited by a GnRH antagonist in a concentration dependent manner (FIG. 8). GnRH-stimulated (10–8 M) inositol phosphate production was inhibited by antagonist 13 with an $IC_{50}$ of $6.7 \times 10^{-9}$ M and by antagonist 5 with an $IC_{50}$ of $1.05 \times 10^{-7}$ M (not shown), giving $\kappa_d$ values of $2.1 \times 10^{-10}$ M and $3.6 \times 10^{-9}$ M respectively (Leslie, F. M., 1987 Pharmacol. Rev. 39:197–247).

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A method for identifying a compound which modulates GnRH-R signal transduction comprising:
    (a) contacting the compound with a genetically engineered cell line that expresses a recombinant GnRH-R encoded for by a nucleic acid molecule that encodes a naturally occurring GnRH-R and that hybridizes to the nucleic acid molecule of SEQ ID NO: 1 or 3;
    (b) incubating the mixture of step (a) in the presence of GnRH, or a GnRH analog, for an interval sufficient for the compound to stimulate or inhibit the signal transduction;
    (c) measuring the signal transduction; and
    (d) comparing the signal transduction activity to that of GnRH-R incubated without the compound, thereby determining whether the compound stimulates or inhibits signal transduction.

2. The method of claim 1 wherein the signal transduction activity of GnRH-R is measured by assaying for the stimulation or inhibition of phospholipase C activity.

3. The method of claim 1 wherein the signal transduction activity of GnRH-R is measured by assaying for the stimulation or inhibition of inositol phosphate (IP) activity.

4. The method of claim 1 wherein the signal transduction activity of GnRH-R is measured by assaying for release of calcium ions from intracellular sources.

* * * * *